(12) United States Patent
Jin et al.

(10) Patent No.: US 11,046,663 B2
(45) Date of Patent: Jun. 29, 2021

(54) ENTECAVIR INTERMEDIATE, SYNTHETIC METHOD THEREOF AND SYNTHETIC METHOD FOR ENTECAVIR

(71) Applicant: Launch-Pharma Technologies, Ltd., Guangzhou (CN)

(72) Inventors: Yehua Jin, Guangzhou (CN); Fayang Qiu, Guangzhou (CN); Hua Xu, Guangzhou (CN); Fang Wang, Guangzhou (CN)

(73) Assignee: Launch-Pharma Technologies, Ltd., Guangdong (CN)

( * ) Notice: Subject to any disclaimer, the term of this patent is extended or adjusted under 35 U.S.C. 154(b) by 0 days.

(21) Appl. No.: 16/759,159

(22) PCT Filed: Sep. 25, 2018

(86) PCT No.: PCT/CN2018/107397
§ 371 (c)(1),
(2) Date: Apr. 24, 2020

(87) PCT Pub. No.: WO2019/080686
PCT Pub. Date: May 2, 2019

(65) Prior Publication Data
US 2020/0255390 A1    Aug. 13, 2020

(30) Foreign Application Priority Data

Oct. 26, 2017  (CN) .......................... 201711014419.2
Dec. 6, 2017   (CN) .......................... 201711279454.7

(51) Int. Cl.
*C07D 303/14*    (2006.01)
*C07D 303/32*    (2006.01)
*C07C 49/537*    (2006.01)
*C07C 49/403*    (2006.01)
*C07D 473/18*    (2006.01)

(52) U.S. Cl.
CPC .......... *C07D 303/14* (2013.01); *C07C 49/403* (2013.01); *C07C 49/537* (2013.01); *C07D 303/32* (2013.01); *C07D 473/18* (2013.01)

(58) Field of Classification Search
CPC .. C07D 303/14; C07D 303/32; C07D 473/18; C07C 49/537; C07C 49/403
USPC ...................................................... 514/263.4
See application file for complete search history.

(56) References Cited

FOREIGN PATENT DOCUMENTS

| CN | 1747959 A   | 3/2006 |
|----|-------------|--------|
| CN | 105524064 A | 4/2016 |
| CN | 103304375 A | 9/2016 |

OTHER PUBLICATIONS

Xu, Hua et al., "Total Synthesis of Entecavir: A Robust Route for Pilot Production", Organic Process Research & Development, vol. 3, No. (22), Feb. 12, 2018, ISSN: 1083-6160.

*Primary Examiner* — Kristin A Vajda
(74) *Attorney, Agent, or Firm* — The Dobrusin Law Firm, PC

(57) ABSTRACT

The disclosure relates to an entecavir intermediate, a synthetic method therefor, and the synthetic method for entecavir by using the intermediate. According to the disclosure, the synthetic methods for entecavir and the intermediate thereof have the advantages of being controllable in chirality, high in yield and product purity, wide in source of raw materials, cheap and available in reagents, simple in reactions, convenient to operate, environmentally friendly, and suitable for industrial amplification production.

20 Claims, No Drawings

ENTECAVIR INTERMEDIATE, SYNTHETIC METHOD THEREOF AND SYNTHETIC METHOD FOR ENTECAVIR

TECHNICAL FIELD

The disclosure relates to the technical field of medicine synthesis, in particular to an entecavir intermediate, a synthetic method therefor and the synthetic method for entecavir.

BACKGROUND ART

Entecavir (a compound of Formula 1), the chemical name of which is 2-amino-1, 9-dihydro-9-[(1S, 3R, 4S)-4-hydroxyl-3-(hydroxymethyl)-2-methylenecyclopentyl]-6H-purin-6-one, firstly received the approval for marketing from the FDA by the original company Bristol Myers Squibb for chronic hepatitis B treatment. It is one of the most important drugs for treating hepatitis B.

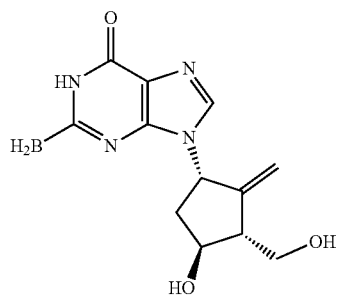

1

The structure of entecavir contains a chiral five-membered carbocyclic ring which has three chiral centers and an exocyclic double bond, and a guanine parent nucleus, so it has a relatively complex chemical structure. Although some synthetic methods of entecavir have been reported, these methods synthesize the chiral five-membered carbocyclic ring by resolution or asymmetric synthesis of the achiral materials to establish the chiral centers. The original route adopts cyclopentadiene as material for asymmetric synthesis and often adopts dangerous reagents such as sodium hydride and lithium hydride, while Dess-Martin reagent, Nysted reagent and the like are quite expensive. The synthetic process involves numerous anhydrous operation reactions, has high requirements for equipment, and is unfavorable to industrial production. This synthetic route is shown as below.

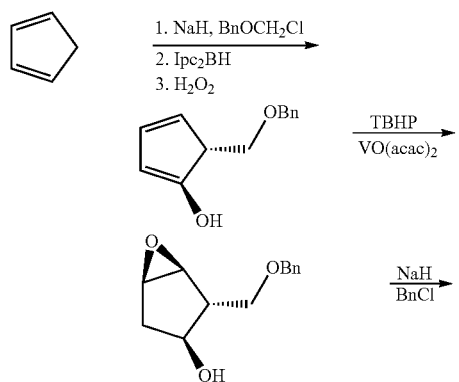

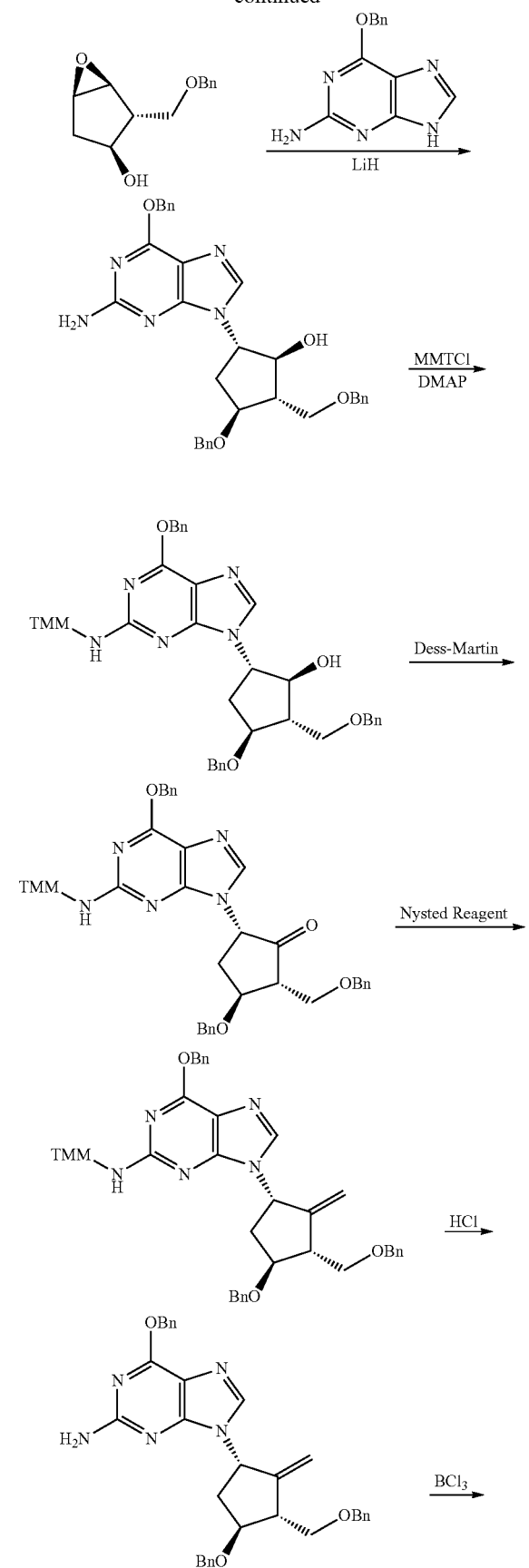

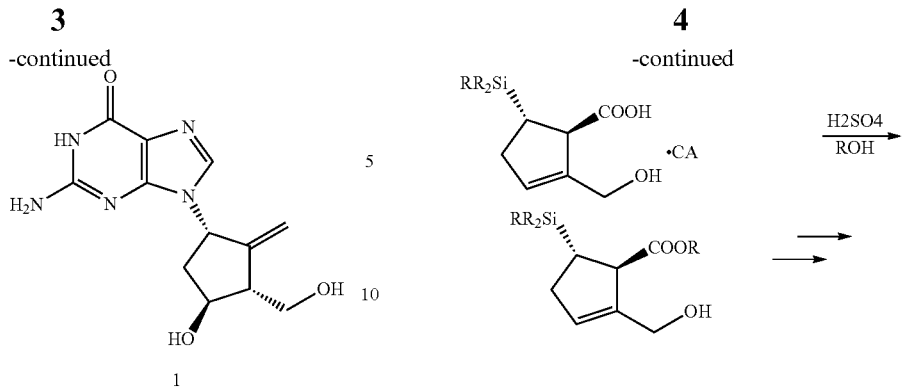

Another method also adopts cyclopentadiene as the raw material, introduces the required functional groups through a [2+2] reaction, carries out the chiral resolution on the carboxylic acid intermediate, obtains compounds of a single enantiomer, and synthesizes the entecavir through other steps. This method causes a waste of raw material in the resolution method, and has low resolution efficiency. This synthetic route is shown as below.

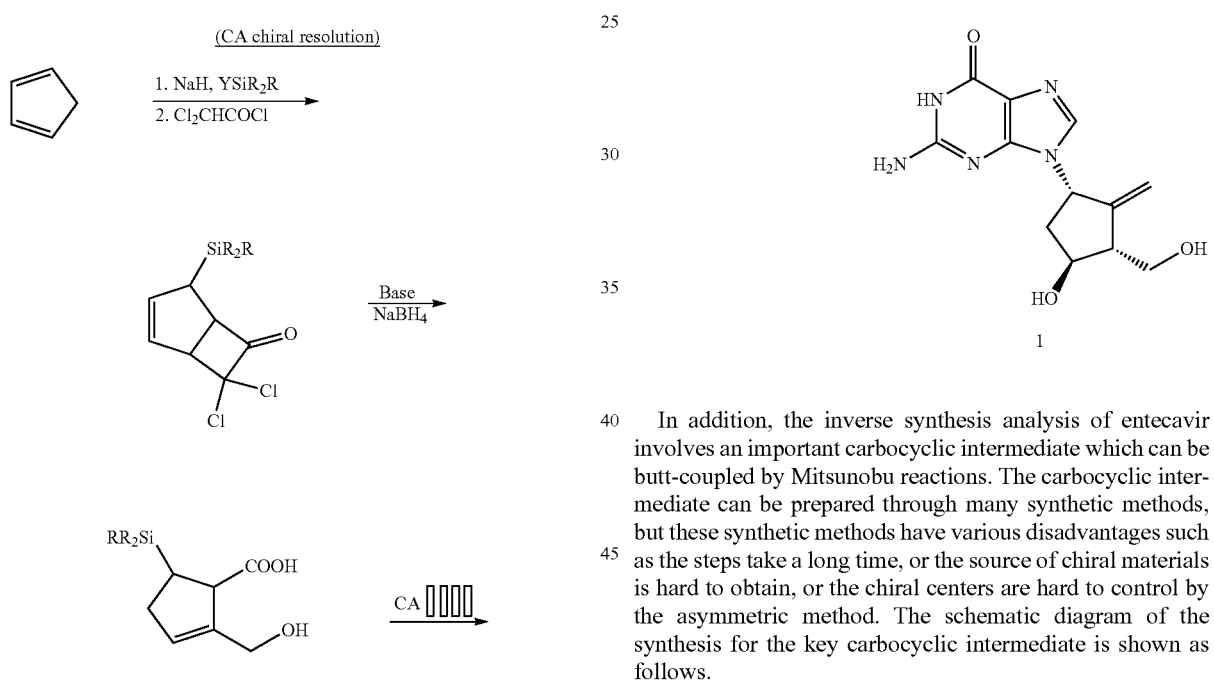

In addition, the inverse synthesis analysis of entecavir involves an important carbocyclic intermediate which can be butt-coupled by Mitsunobu reactions. The carbocyclic intermediate can be prepared through many synthetic methods, but these synthetic methods have various disadvantages such as the steps take a long time, or the source of chiral materials is hard to obtain, or the chiral centers are hard to control by the asymmetric method. The schematic diagram of the synthesis for the key carbocyclic intermediate is shown as follows.

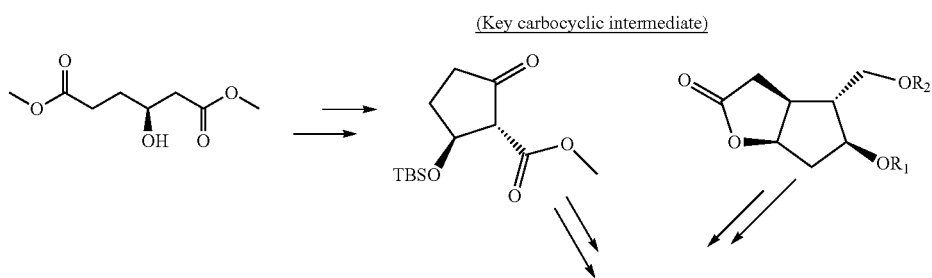

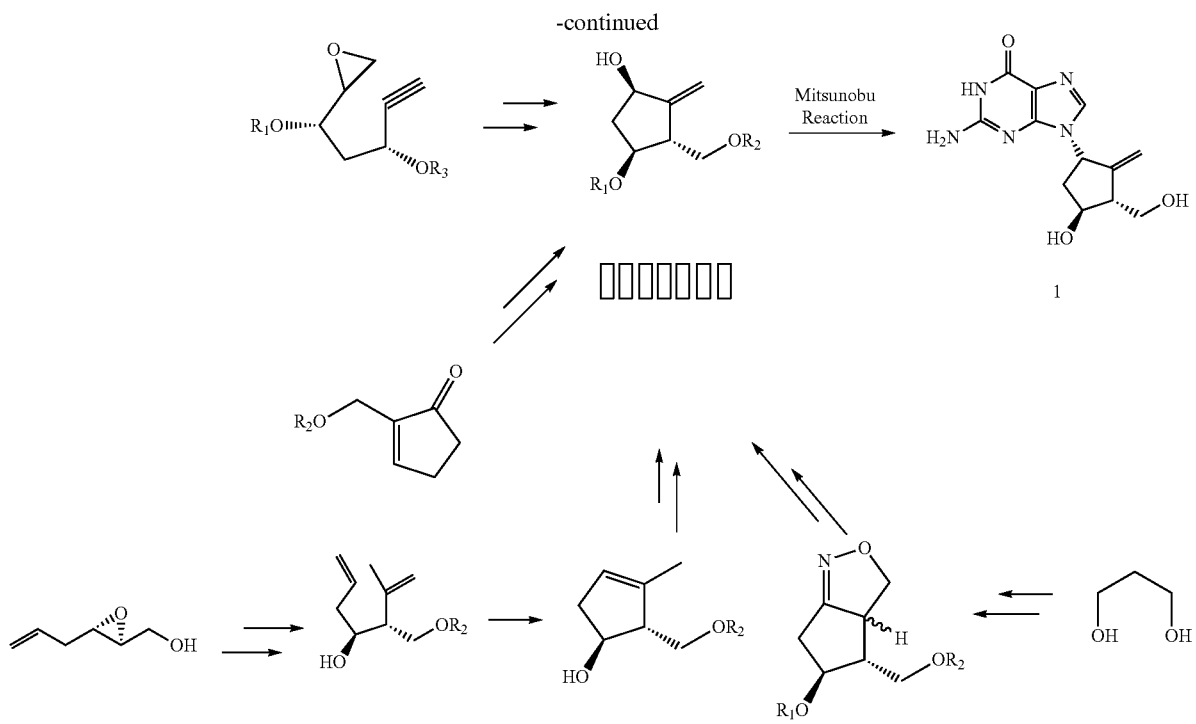

Therefore, all the existing methods for preparing the entecavir have disadvantages, and it is needed to develop a method for preparing the entecavir which is wide in source of raw materials, cheap and available in reagents, convenient to operate, environmentally friendly, high in optical purity, and suitable for industrial amplification production.

SUMMARY OF THE INVENTION

Based on the above, a new intermediate for preparing entecavir is provided.

The technical solution is as follows.

An entecavir intermediate or an intermediate composition for preparing entecavir, in which the entecavir intermediate or the intermediate composition is selected from at least one of the following compounds:

4

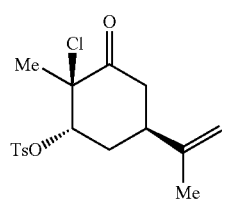

5

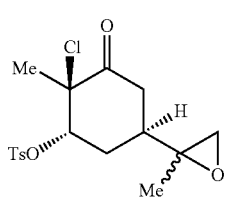

6

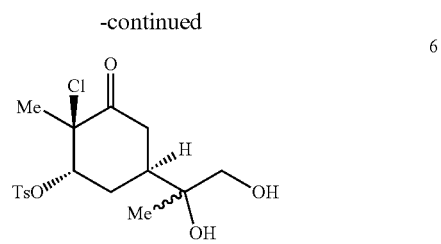

7

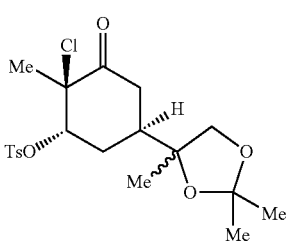

8

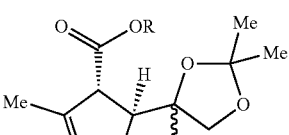

9

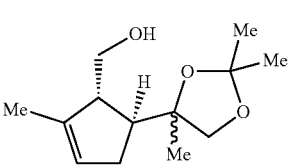

-continued

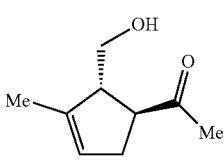
10

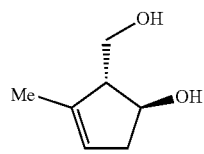
11

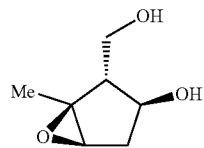
12 in which R is methyl or ethyl.

The invention also provides a synthetic method for the entecavir intermediate.

The technical solutions are as follows.

A synthetic method for the entecavir intermediate having the structure shown in Formula 10 comprises the following steps of:

(c) reacting the compound of Formula 3 with an esterification reagent in the presence of the base to produce the compound of Formula 4;

(d) epoxide reacting the compound of Formula 4 in the presence of an epoxide reagent to produce the compound of Formula 5;

(e) epoxide ring-opening reacting the compound of Formula 5 under the action of an acid to produce the compound of Formula 6;

(f) dihydroxy acetone reacting the compound of Formula 6 with a hydroxyl acetonide protection reagent under the action of an acid catalyst to produce the compound of Formula 7;

(g) Favorskii rearrangement reacting the compound of Formula 7 under the action of the base to produce the compound of Formula 8;

(h) reduction reacting the compound of Formula 8 under the action of a reducing agent to produce the compound of Formula 9;

(i) removing the hydroxyl protecting group of the compound of Formula 9 under the catalysis of the acid, and then oxidation reacting under the action of an oxidizing agent to produce the compound of Formula 10;

the reaction formulas are as follows:

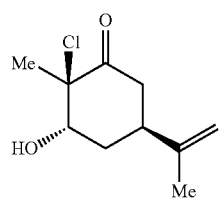
3

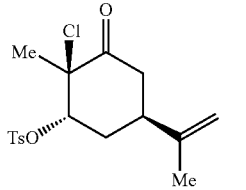
4

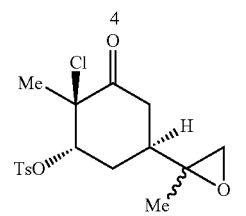
5

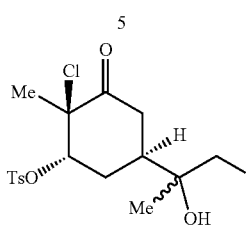
6

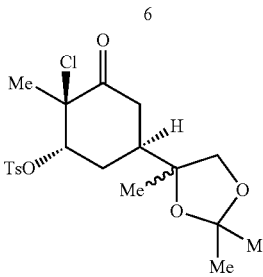
7

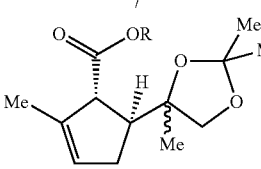
8

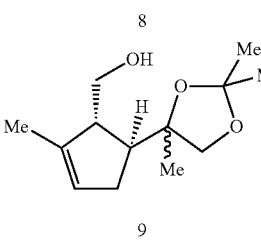
9

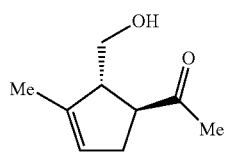
10 in which R is methyl or ethyl.

In some embodiments, the synthetic method for the entecavir intermediate having the structure shown in Formula 10 further comprises the following steps of:

(a) epoxide reacting a D(+)-carvone under the action of the base and the oxidizing agent to produce the compound of Formula 2;

(b) chlorination ring-opening reacting the compound of Formula 2 under the action of the acid and a chloride reagent to produce the compound of Formula 3; and the reaction formulas are as follows.

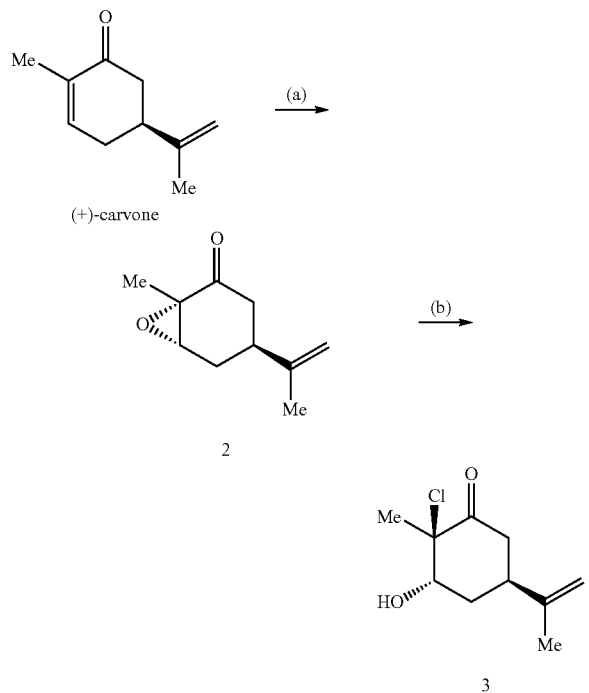

In some embodiments, the reaction solvent in step (a) is methanol, the base is sodium hydroxide, the oxidizing agent is hydrogen peroxide, the reaction temperature of the epoxide reaction is −5 to 10 DEG C., and the molar ratio of the D(+)-carvone, the base and the oxidizing agent is 1:(0.1 to 0.3):(0.8 to 1.4); and/or the reaction solvent in step (b) is tetrahydrofuran, the acid is trifluoroacetic acid, the chloride reagent is anhydrous lithium chloride, the reaction temperature of the chlorination ring-opening reaction is 0 to 35 DEG C., and the molar ratio of the compound of Formula 2, the acid and the chloride reagent is 1:(0.8 to 2):(0.8 to 2).

In some embodiments, the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or the reaction solvent in step (e) is a combination of water and organic solvent, the organic solvent is tetrahydrofuran and/or 1,4-dioxane, the volume ratio of water to the organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or the reaction in step (f) is carried out in the absence of a solvent, or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or the reaction solvent in step (g) is an alcohol solvent or a combination of the alcohol solvent and an ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or the reaction solvent in step (i) is selected from methanol, ethanol, tetrahydrofuran, 1,4-dioxane and water, the acid is selected from p-toluenesulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2):(0.8 to 3).

In some embodiments, the reaction temperature of the reaction in step (c) is 10 to 30 DEG C., the base is selected from 4-dimethylaminopyridine, and the molar ratio of the compound of Formula 3, 4-dimethylaminopyridine, and p-toluenesulfonyl chloride is 1:(1.5to2):(1.2to 1.8).

In some embodiments, the temperature of the epoxide reaction in step (d) is 20 to 30 DEG C., and the molar ratio of the compound of Formula 4 to the epoxide reagent is 1:(1 to 1.2).

In some embodiments, the temperature of the epoxide ring-opening reaction in step (e) is 20 to 30 DEG C., and the molar ratio of the compound of Formula 5 to the acid is 1:(0.8 to 1).

In some embodiments, the reaction temperature of the dihydroxy acetone reaction in step (f) is 20 to 30 DEG C., and the molar ratio of the compound of Formula 6, the hydroxyl acetonide protection reagent and the acid catalyst is 1:(1 to 1.5):(0.02 to 0.06).

In some embodiments, the reaction temperature of the Favorskii rearrangement reaction in step (g) is −5 to 30 DEG C., and the molar ratio of the compound of Formula 7 to the base is 1:(2.5 to 3.5).

In some embodiments, the reaction temperature of the reaction solvent in the reduction reaction in step (h) is −5 to 15 DEG C., and the molar ratio of the compound of Formula 8 to the reducing agent is 1:(1 to 1.3).

In some embodiments, the reaction temperature in step (i) is 20 to 30 DEG C., and the molar ratio of the compound of Formula 9, the acid, and the oxidizing agent is 1:(0.8 to 1.5):(0.8 to 1.5).

A synthetic method for the entecavir intermediate having the structure shown in Formula 12 comprises the following steps of:

(j) Baeyer-Villiger oxidative rearrangement reacting the compound of Formula 10 under the action of a base and peroxide to produce the compound of Formula 11;

(k) epoxide reacting the compound of Formula 11 under the action of a catalyst and the oxidizing agent to produce the compound of Formula 12; and the reaction formulas are as follows.

(h) reduction reacting the compound of Formula 8 under the action of the reducing agent to produce the compound of Formula 9;

(i) removing the hydroxyl protecting group of the compound of Formula 9 under the catalysis of the acid, and then oxidation reacting under the action of the oxidizing agent to produce the compound of Formula 10;

(j) Baeyer-Villiger oxidative rearrangement reacting the compound of Formula 10 under the action of the base and peroxide to produce the compound of Formula 11;

(k) epoxide reacting the compound of Formula 11 under the action of the catalyst and the oxidizing agent to produce the compound of Formula 12; and the reaction formulas are as follows:

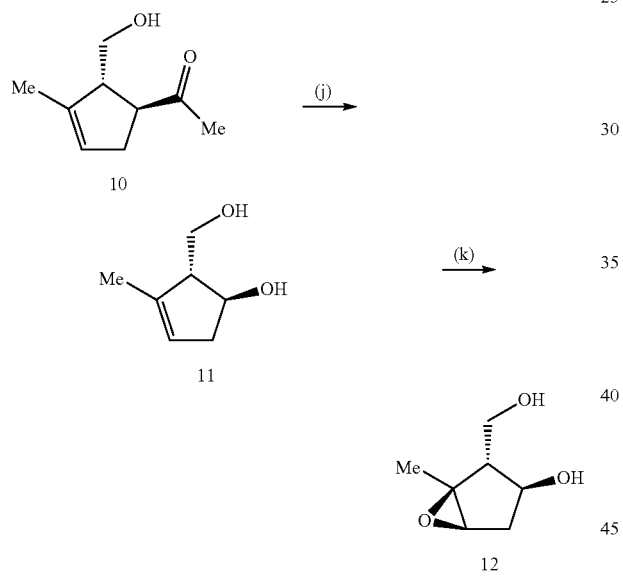

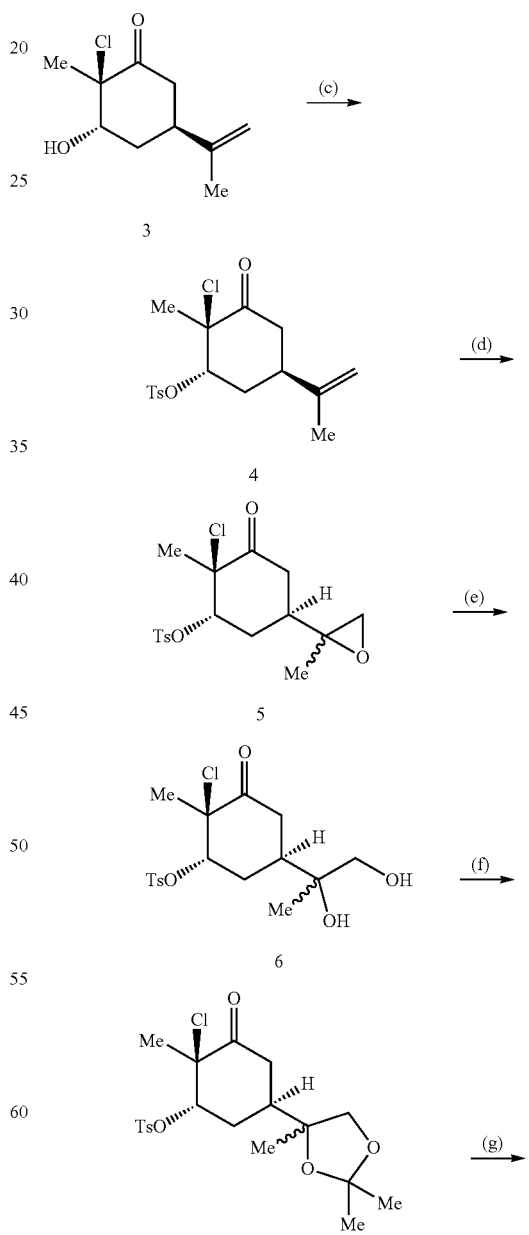

In some embodiments, the synthetic method for the entecavir intermediate having the structure shown in Formula 12 comprises the following steps of:

(c) reacting the compound of Formula 3 with the esterification reagent in the presence of the base to produce the compound of Formula 4;

(d) epoxide reacting the compound of Formula 4 in the presence of an epoxide reagent to produce the compound of Formula 5;

(e) epoxide ring-opening reacting the compound of Formula 5 under the action of the acid to produce the compound of Formula 6;

(f) dihydroxy acetone reacting the compound of Formula 6 with a hydroxyl acetonide protection reagent under the action of the acid catalyst to produce the compound of Formula 7;

(g) Favorskii rearrangement reacting the compound of Formula 7 under the action of the base to produce the compound of Formula 8;

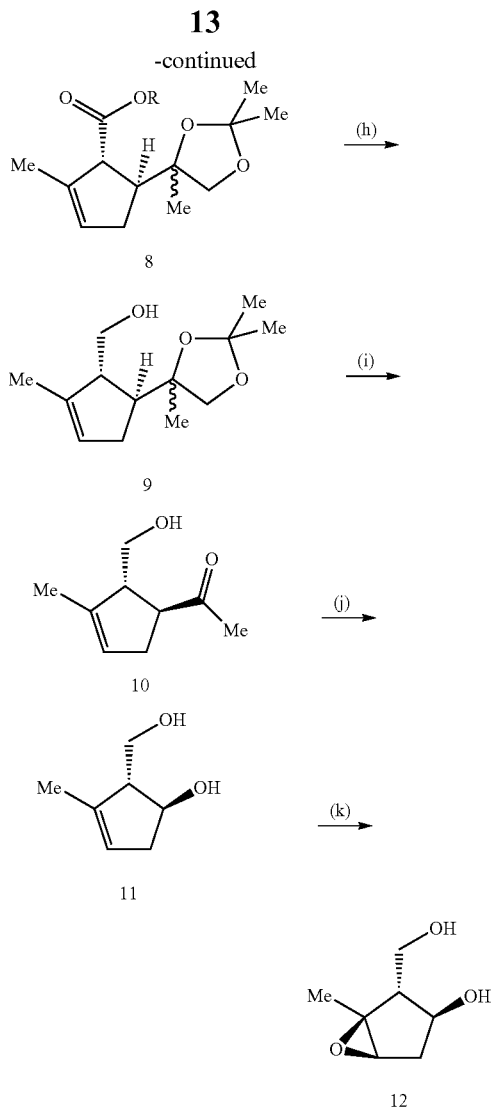

in which R is methyl or ethyl.

In some embodiments, the synthetic method for the entecavir intermediate having the structure shown in Formula 12 further comprises the following steps of:

(a) epoxide reacting the D(+)-carvone under the action of the base and the oxidizing agent to produce the compound of Formula 2;

(b) chlorination ring-opening reacting the compound of Formula 2 under the action of the acid and the chloride reagent to produce the compound of Formula 3; and the reaction formulas are as follows.

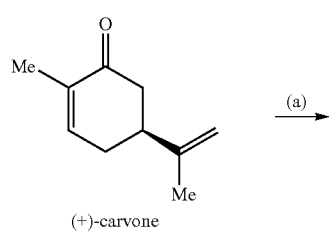

In some embodiments, the reaction solvent in step (a) is methanol, the base is sodium hydroxide, the oxidizing agent is hydrogen peroxide, the reaction temperature of the epoxide reaction is −5 to 10 DEG C., and the molar ratio of the D(+)-carvone, the base and the oxidizing agent is 1:(0.1 to 0.3):(0.8 to 1.4); and/or the reaction solvent in step (b) is tetrahydrofuran, the acid is trifluoroacetic acid, the chloride reagent is anhydrous lithium chloride, the reaction temperature of the chlorination ring-opening reaction is 0 to 35 DEG C., and the molar ratio of the compound of Formula 2, the acid and the chloride reagent is 1:(0.8 to 2):(0.8 to 2).

In some embodiments, the reaction solvent in step (j) is selected from methanol, ethanol, tert-butanol and isopropanol, the base is sodium hydroxide and/or potassium hydroxide, the peroxide is selected from hydrogen peroxide, hydrogen peroxide complex and tert-butyl hydroperoxide, the temperature of the Baeyer-Villiger oxidative rearrangement reaction is 0 to 100 DEG C., and the molar ratio of the compound of Formula 10, the base and the peroxide is 1:(1 to 20):(1 to 20); and/or the reaction solvent in step (k) is selected from dichloromethane, toluene and 1,2-dichloroethane, the catalyst is vanadyl acetylacetonate, the oxidizing agent is tert-butyl hydroperoxide, the reaction temperature of the epoxide reaction is −25 to 25 DEG C., and the molar ratio of the compound of Formula 11, the catalyst and the oxidizing agent is 1:(0.001 to 0.2):(1 to 2).

In some embodiments, the temperature of the Baeyer-Villiger oxidative rearrangement reaction in step (j) is 55 to 75 DEG C., and the molar ratio of the compound of Formula 10, the base, and the peroxide is 1:(2 to 3.5):(5 to 8).

In some embodiments, the reaction temperature of the epoxide reaction in step (k) is −10 to 10 DEG C., and the molar ratio of the compound of Formula 11, the catalyst and the oxidizing agent is 1:(0.03 to 0.06):(1 to 1.5).

In some embodiments, the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or the reaction solvent in step (e) is a combination of water and organic solvent, the organic solvent is tetrahydrofuran and/or 1,4-dioxane, the volume ratio of water to the organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or the reaction in step (f) is carried out in the absence of the solvent, or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or the reaction solvent in step (g) is the alcohol solvent or a combination of the alcohol solvent and the ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or the reaction solvent in step (i) is selected from methanol, ethanol, tetrahydrofuran, 1,4-dioxane and water, the acid is selected from p-toluenesulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2):(0.8 to 3).

In some embodiments, the reaction temperature of the reaction in step (c) is 10 to 30 DEG C., the base is selected from 4-dimethylaminopyridine, and the molar ratio of the compound of Formula 3, 4-dimethylaminopyridine and p-toluenesulfonyl chloride is 1:(1.5 to 2):(1.2 to 1.8).

In some embodiments, the temperature of the epoxide reaction in step (d) is 20 to 30 DEG C., and the molar ratio of the compound of Formula 4 to the epoxide reagent is 1:(1 to 1.2).

In some embodiments, the temperature of the epoxide ring-opening reaction in step (e) is 20 to 30 DEG C., and the molar ratio of the compound of Formula 5 to the acid is 1:(0.8 to 1).

In some embodiments, the reaction temperature of the dihydroxy acetone reaction in step (f) is 20 to 30 DEG C., and the molar ratio of the compound of Formula 6, the hydroxyl acetonide protection reagent and the acid catalyst is 1:(1 to 1.5):(0.02 to 0.06).

In some embodiments, the reaction temperature of the Favorskii rearrangement reaction in step (g) is −5 to 30 DEG C., and the molar ratio of the compound of Formula 7 to the base is 1:(2.5 to 3.5).

In some embodiments, the reaction temperature of the reaction solvent in the reduction reaction in step (h) is −5 to 15 DEG C., and the molar ratio of the compound of Formula 8 to the reducing agent is 1:(1 to 1.3).

In some embodiments, the reaction temperature in step (i) is 20 to 30 DEG C., and the molar ratio of the compound of Formula 9, the acid and the oxidizing agent is 1:(0.8 to 1.5):(0.8 to 1.5).

The invention also provides a method for synthesizing the entecavir.

The technical solutions are as follows.

A method for synthesizing the entecavir comprises the following steps:

(l) protecting hydroxyl in the compound of Formula 12 to produce the compound of Formula 13;

(m) epoxide isomerization reacting the compound of Formula 13 with an epoxide isomerization reagent to produce the compound of Formula 14;

(n) reacting the compound of Formula 14 with the compound of Formula 16 under Mitsunobu reaction conditions to produce the compound of Formula 15;

(o) carrying out a hydrolysis reaction on the compound of Formula 15, removing the hydroxyl protecting group and the amino protecting group thereof, and producing the compound of Formula 1 to give entecavir; and the reaction formulas are as follows:

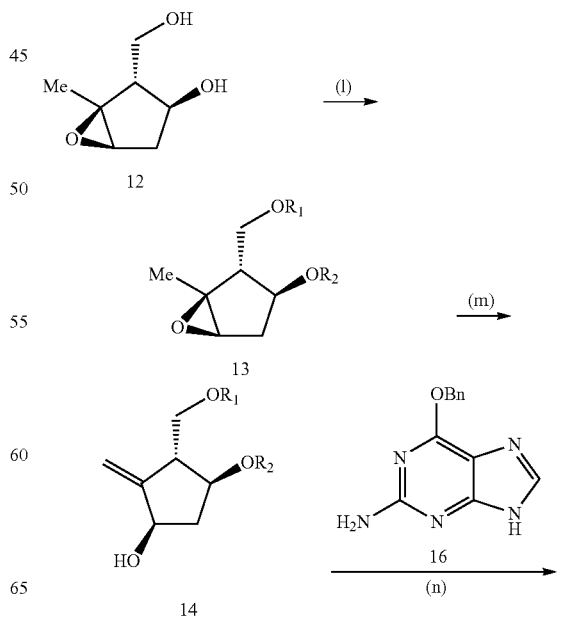

-continued

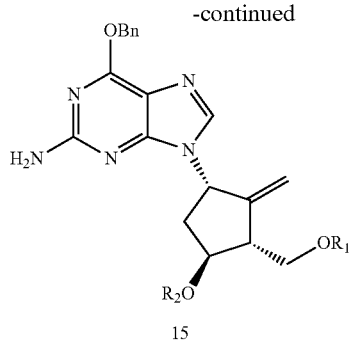
15

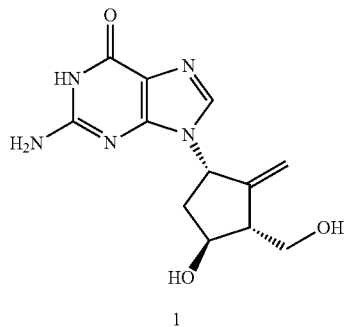
1 wherein R1 and R2 are protecting groups of the hydroxyl, and R1 and R2 are each independently selected from the protecting groups of the following classes: (1) silicyl, (2) alkyl, (3) alkoxymethyl, (4) benzyloxymethyl and substituted benzyloxymethyl, (5) alkoxyethyl, (6) benzyl and benzyl substituted by a phenyl ring, (7) acyl, (8) alkoxyacyl, and (9) siloxymethyl.

In some embodiments, the method for synthesizing the entecavir further comprises the following steps:

(c) reacting the compound of Formula 3 with an esterification reagent in the presence of the base to produce the compound of Formula 4;

(d) epoxide reacting the compound of Formula 4 in the presence of an epoxide reagent to produce the compound of Formula 5;

(e) epoxide ring-opening reacting the compound of Formula 5 under the action of the acid to produce the compound of Formula 6;

(f) dihydroxy acetone reacting the compound of Formula 6 with a hydroxyl acetonide protection reagent under the action of the acid catalyst to produce the compound of Formula 7;

(g) Favorskii rearrangement reacting the compound of Formula 7 under the action of the base to produce the compound of Formula 8;

(h) reduction reacting the compound of Formula 8 under the action of a reducing agent to produce the compound of Formula 9;

(i) removing a hydroxyl protecting group of the compound of Formula 9 under the catalysis of the acid, and then oxidation reacting under the action of the oxidizing agent to produce the compound of Formula 10;

(j) Baeyer-Villiger oxidative rearrangement reacting the compound of Formula 10 under the action of the base and peroxide to produce the compound of Formula 11;

(k) epoxide reacting the compound of Formula 11 under the action of the catalyst and the oxidizing agent to produce the compound of Formula 12; and the reaction formulas are as follows:

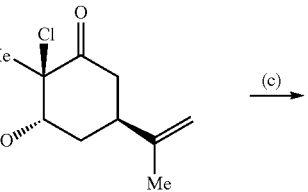
3

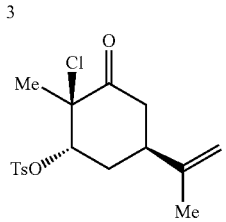
4

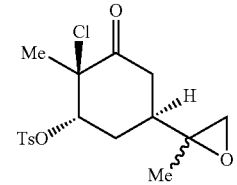
5

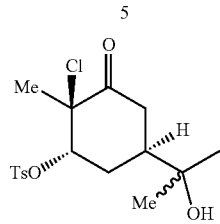
6

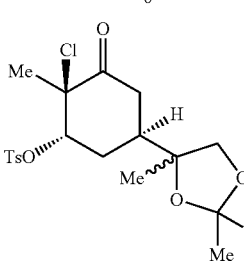
7

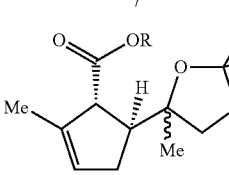
8

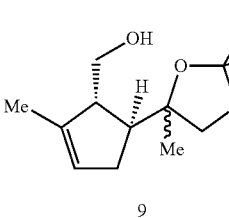
9

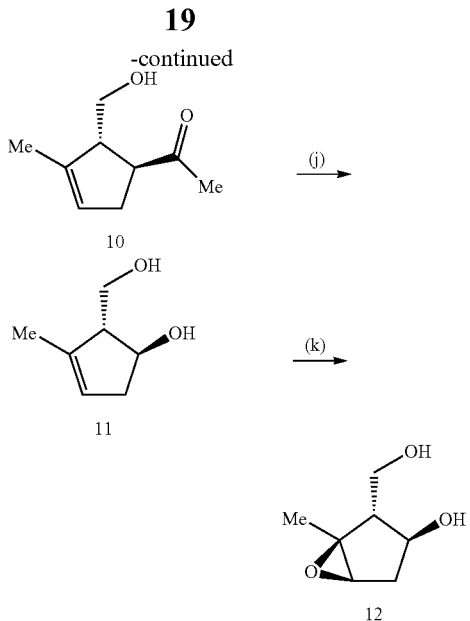

in which R is methyl or ethyl.

In some embodiments, R1 and R2 are each independently selected from: trimethylsilyl, tert-butyldiphenylsilyl, tert-butyldimethylsilyl, triethylsilyl, triisopropylsilyl, methyl, methoxymethyl, 2-methoxyethoxymethyl, benzyloxymethyl, p-methoxybenzyloxymethyl, p-nitrobenzyloxymethyl, o-nitrobenzyloxymethyl, 2-(trimethylsilyl)ethoxymethyl, tetrahydropyran-2-yl, 1-ethoxyethyl, benzyl, p-methoxybenzyl, 3,4-dimethoxybenzyl, trityl, formyl, acetyl, benzoyl, p-phenylbenzoyl, methoxyacyl, ethoxyacyl, 9-fluorenylmethoxyacyl, and tert-butoxyacyl.

In some embodiments, protecting the hydroxyl in the compound of Formula 12 in step (1) comprises: reacting the compound of Formula 12 with a hydroxyl protection reagent; R1 and R2 are each independently selected from: trimethylsilyl, tert-butyldiphenylsilyl, tert-butyldimethylsilyl, triethylsilyl, triisopropylsilyl, methyl, methoxymethyl, 2-methoxyethoxymethyl, benzyloxymethyl, p-methoxybenzyloxymethyl, p-nitrobenzyloxymethyl, o-nitrobenzyloxymethyl, 2-(trimethylsilyl)ethoxymethyl, benzyl, p-methoxybenzyl, 3,4-dimethoxybenzyl, trityl, formyl, acetyl, benzoyl, p-phenylbenzoyl, methoxyacyl, ethoxyacyl, 9-fluorenylmethoxyacyl, and tert-butoxyacyl, the hydroxyl protection reagent is R1X and R2X in which X is a leaving group and is selected from halogen or triflate, reacting the compound of Formula 12 with the hydroxyl protection reagent is reacting the compound of Formula 12 with R1X and R2X in the presence of the base and/or the catalyst, the base is selected from at least one of triethylamine, diisopropylethylamine, imidazole, pyridine, sodium hydroxide, potassium hydroxide, sodium hydride, lithium hydride, sodium bis(trimethylsilyl)amide, and lithium bis(trimethylsilyl)amide, and the catalyst is selected from at least one of 4-dimethylaminopyridine, tetrabutylammonium bromide, tetrabutylammonium hydrogen sulfate and tetrabutylammonium iodide; or R1 and R2 are each independently selected from tetrahydropyran-2-yl, the hydroxyl protection reagent is dihydropyran, reacting the compound of Formula 12 with the hydroxyl protection reagent is reacting the compound of Formula 12 with the dihydropyran under acid catalysis, and the acid is selected from p-toluene sulfonic acid and pyridinium p-toluenesulfonate; or R1 and R2 are each independently selected from 1-ethoxyethyl, the hydroxyl protection reagent is ethyl vinyl ether, reacting the compound of Formula 12 with the hydroxyl protection reagent is reacting the compound of Formula 12 with the ethyl vinyl ether under acid catalysis, and the acid is selected from the p-toluene sulfonic acid and the pyridinium p-toluenesulfonate.

In some embodiments, the hydroxyl protection reagent in step (1) is tert-butyldimethylsilyl chloride, the compound of Formula 12 reacts with the hydroxyl protection reagent under the action of the base and the catalyst, the reaction solvent is selected from methylene chloride and N,N-dimethylformamide, the base is selected from triethylamine and imidazole, the catalyst is 4-dimethylaminopyridine, the reaction temperature is 0 to 50 DEG C., and the molar ratio of the compound of Formula 12, the base, the catalyst and the tert-butyldimethylsilyl chloride is 1:(2 to 3):(0.05 to 0.2):(2 to 3).

In some embodiments, the reaction temperature in step (1) is 5 to 30 DEG C., the base is imidazole, the catalyst is 4-dimethylaminopyridine, and the molar ratio of the compound of Formula 12, the tert-butyldimethylsilyl chloride, the imidazole and the 4-dimethylaminopyridine is 1:(2 to 2.5):(2.2 to 2.5):(0.1 to 0.2).

In some embodiments, the reaction solvent in step (m) is selected from toluene, xylene, tetrahydrofuran, methyl tertiary butyl ether and diethyl ether, the epoxide isomerization reagent is selected from lithium diisopropylamide, 2,2,6,6-tetramethylpiperidine lithium, aluminum complexes generated in situ by lithium diisopropylamide and diethylaluminum chloride, aluminum complexes generated in situ by 2,2,6,6-tetramethylpiperidine lithium and diethylaluminum chloride, aluminum isopropoxide, camphorsulfonic acid and p-methylbenzene sulfonic acid, and the reaction temperature of the epoxide isomerization reaction is −25 to 110 DEG C.

In some embodiments, the reaction solvent in step (m) is toluene, the epoxide isomerization reagent is the aluminum complexes generated in situ by 2,2,6,6-tetramethylpiperidine lithium and diethylaluminum chloride, the reaction temperature of the epoxide isomerization reaction is −10 to 5 DEG C., and the molar ratio of the compound of Formula 13 to the epoxide isomerization reagent is 1:(1 to 3).

In some embodiments, the molar ratio of the compound of Formula 14 to the compound of Formula 16 in step (n) is 1:(1 to 2).

In some embodiments, the molar ratio of the compound of Formula 14 to the compound of Formula 16 in step (n) is 1:(1.3 to 1.6).

In some embodiments, R1 and R2 are both tert-butyldimethylsilyl, the reaction solvent of the hydrolysis reaction in step (o) is tetrahydrofuran and water, the hydrolysis reaction is carried out under the action of dilute hydrochloric acid, and the reaction temperature is 10 to 70 DEG C.

In some embodiments, the reaction solvent of the hydrolysis reaction in step (o) is tetrahydrofuran and water, the hydrolysis reaction is carried out under the action of dilute hydrochloric acid, and the reaction temperature is 50 to 60 DEG C.

In some embodiments, the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or the reaction solvent in step (e) is a combination of water and organic solvent, the organic solvent is tetrahydrofuran and/or 1,4-dioxane, the volume ratio of water to the organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or the reaction in step (f) is carried out in the absence of the solvent or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or the reaction solvent in step (g) is the alcohol solvent or a combination of the alcohol solvent and the ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or the reaction solvent in step (i) is selected from methanol, ethanol, tetrahydrofuran, 1,4-dioxane and water, the acid is selected from p-toluene sulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2):(0.8 to 3); and/or the reaction solvent in step (j) is selected from methanol, ethanol, tert-butanol and isopropanol, the base is sodium hydroxide and/or potassium hydroxide, the peroxide is selected from hydrogen peroxide, hydrogen peroxide complex and tert-butyl hydroperoxide, the temperature of the Baeyer-Villiger oxidative rearrangement reaction is 0 to 100 DEG C., and the molar ratio of the compound of Formula 10, the base and the peroxide is 1:(1 to 20):(1 to 20); and/or the reaction solvent in step (k) is selected from dichloromethane, toluene and 1,2-dichloroethane, the catalyst is vanadyl acetylacetonate, the oxidizing agent is tert-butyl hydroperoxide, the reaction temperature of the epoxide reaction is −25 to 25 DEG C., and the molar ratio of the compound of Formula 11, the catalyst and the oxidizing agent is 1:(0.001 to 0.2):(1 to 2).

In some embodiments, the reaction temperature of the reaction in step (c) is 10 to 30 DEG C., the base is selected from 4-dimethylaminopyridine, and the molar ratio of the compound of Formula 3, 4-dimethylaminopyridine and p-toluenesulfonyl chloride is 1:(1.5 to 2):(1.2 to 1.8).

In some embodiments, the temperature of the epoxide reaction in step (d) is 20 to 30 DEG C., and the molar ratio of the compound of Formula 4 to the epoxide reagent is 1:(1 to 1.2).

In some embodiments, the temperature of the epoxide ring-opening reaction in step (e) is 20 to 30 DEG C., and the molar ratio of the compound of Formula 5 to the acid is 1:(0.8 to 1).

In some embodiments, the reaction temperature of the dihydroxy acetone reaction in step (f) is 20 to 30 DEG C., and the molar ratio of the compound of Formula 6, the hydroxyl acetonide protection reagent and the acid catalyst is 1:(1 to 1.5):(0.02 to 0.06).

In some embodiments, the reaction temperature of the Favorskii rearrangement reaction in step (g) is −5 to 30 DEG C., and the molar ratio of the compound of Formula 7 to the base is 1:(2.5 to 3.5).

In some embodiments, the reaction temperature of the reaction solvent in the reduction reaction in step (h) is −5 to 15 DEG C., and the molar ratio of the compound of Formula 8 to the reducing agent is 1:(1 to 1.3).

In some embodiments, the reaction temperature in step (i) is 20 to 30 DEG C., and the molar ratio of the compound of Formula 9, the acid and the oxidizing agent is 1:(0.8 to 1.5):(0.8 to 1.5).

In some embodiments, the temperature of the Baeyer-Villiger oxidative rearrangement reaction in step (j) is 55 to 75 DEG C., and the molar ratio of the compound of Formula 10, the base, and the peroxide is 1:(2 to 3.5):(5 to 8).

In some embodiments, the reaction temperature of the epoxide reaction in step (k) is −10 to 10 DEG C., and the molar ratio of the compound of Formula 11, the catalyst and the oxidizing agent is 1:(0.03 to 0.06):(1 to 1.5).

It can be understood that any step of (a) to (n) of above method for synthesizing entecavir can directly use the reaction product obtained in the previous step as a raw material for the subsequent reaction to produce entecavir. For example, entecavir can be prepared by using the compound of Formula 7 as the raw material and performing steps (g) to (o) as described above, or by using the compound of Formula 8 as the raw material and performing steps (h) to (o) as described above.

It can be understood that the corresponding steps in the above method for synthesizing entecavir can be used to synthesize the corresponding entecavir intermediate. For example, intermediate 4 can be synthesized using step (c), intermediate 8 can be synthesized using steps (c) to (g), intermediate 10 can be synthesized using steps (c) to (i), and intermediate 11 can be synthesized using steps (c) to (j), and so on. It also can be understood that the reaction product obtained in any step of (a) to (j) can be directly used as the raw material for the subsequent reaction to prepare the above-described entecavir intermediate. For example, intermediate 11 can be prepared by using the compound of Formula 7 as the raw material and performing above-described steps (g) to (j), or by using the compound of Formula 8 as the raw material and performing above-described steps (h) to (j).

The entecavir intermediate and the synthetic method thereof as well as the method for synthesizing the entecavir in the present invention have the following advantages and beneficial effects.

The present invention prepares and obtains a series of new entecavir intermediate, provides an optimized synthetic method of the intermediate, and the entecavir can be prepared in a high yield with the intermediate as raw materials. According to the invention, the synthetic methods of entecavir and the intermediate thereof have the advantages of being controllable in chirality, high in yield and product purity. The obtained finished products of the intermediate and entecavir have high optical purity, and are wide in source of raw materials, cheap and available in reagents, simple in reactions, convenient to operate, environmentally friendly, and suitable for industrial amplification production.

Embodiments

The entecavir intermediate, the synthetic method thereof, and the synthetic method for entecavir according to the present invention are further described below through specific embodiments. It should be understood that the following embodiments are merely provided for a better understanding of the invention and are not intended to limit the scope of the invention in any way.

Embodiment 1 Preparation of Intermediate Compound 4

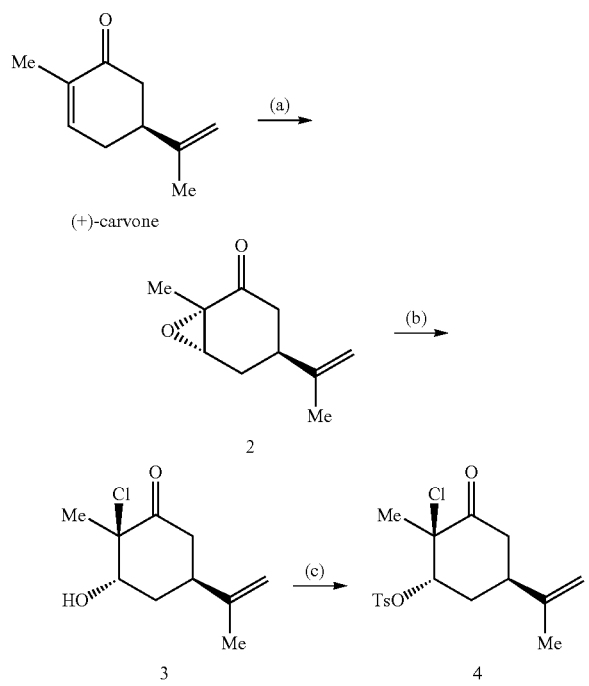

Step (a): D(+)-carvone (3.00 kg, 19.97 mol, 1.00 eq) and methanol (15 L) were added to a 50 L reaction kettle, stirred for 8 minutes, and cooled to 0 DEG C. NaOH solution (1 L, 4 mol/L, 3.99 mol, 0.20 eq) was slowly added, then hydrogen peroxide (2.4 kg, 30% wt, 21.97 mol, 1.10 eq) was added dropwise with the inner temperature being controlled to be no more than 5 DEG C. during the dropwise adding process. The stirring was continued at 0 to 5 DEG C. for about 10 hours after the dropwise adding while TLC monitoring was performed, anhydrous sodium sulfate solid (0.60 kg) was added after the raw materials disappeared and was stirred for 0.5 hour. After testing the absence of oxidizability with starch potassium iodide test paper, the reaction solution was concentrated under reduced pressure and methanol was recovered. The remaining liquid was stirred for 20 minutes after adding with water (5 L) and methylene chloride (15 L), and then the liquid was separated. The aqueous layer was extracted with methylene chloride (10 L×2), the organic layers were combined, and the saturated sodium chloride solution (5 L) was added for washing. After the liquid was separated, the organic layers were concentrated under reduced pressure and the methylene chloride was recovered. The residue was dissolved with petroleum ether (16 L), and was filtered under reduced pressure via Buchner funnel [with a pad of silica gel (0.50 kg)]. The filter cake was washed with petroleum ether/ethyl acetate (20:1, 15 L) and the filtrate was concentrated under reduced pressure to constant weight to give compound 2 (4.10 kg, yield: 124.2%) as a light yellow oil, $R_f$=0.54 (petroleum ether/ethyl acetate =10:1).

$[\alpha]_D$=−60.7° (c=1.03, MeOH);
$^1$H NMR (500 MHz, CDCl$_3$) δ 4.78 (s, 1H), 4.71 (s, 1H), 3.43 (d, J=2.6 Hz, 1H), 2.71 (td, J=11.2, 5.3 Hz, 1H), 2.58 (dd, J=17.6, 4.5 Hz, 1H), 2.36 (d, J=14.8 Hz, 1H), 2.02 (dd, J=17.6, 11.6 Hz, 1H), 1.93-1.84 (m, 1H), 1.70 (s, 3H), 1.40 (s, 3H);
$^{13}$C NMR (126 MHz, CDCl$_3$) δ 205.5, 146.5, 110.6, 61.5, 58.7, 41.9, 35.2, 28.9, 20.7, 15.4.

Step (b): The compound 2 (4.10 kg, 24.67 mol, 1 eq) and tetrahydrofuran (20 L) were added to the 50 L reaction kettle, stirred for 8 minutes, and cooled to 2 DEG C. Anhydrous lithium chloride (0.93 kg, 21.97 mol, 0.89 eq) was added, then trifluoroacetic acid (2.51 kg, 21.97 mol, 0.89 eq) was added dropwise with the inner temperature being controlled to be 0 to 10 DEG C. during the dropwise adding process. After the dropwise adding, the reaction temperature was raised to room temperature and the stirring was continued for about 8 hours, sodium bicarbonate solution (dissolving 1.8 kg sodium bicarbonate in 10 L water) was added for neutralization. The stirring was continued for 0.5 hour after the pH was 7 to 8. The tetrahydrofuran was recovered under reduced pressure, the remaining liquid was added with ethyl acetate (20 L) for stirring and liquid separation, and the aqueous layer was extracted with ethyl acetate (10 L×2). The organic layers were combined and washed with the saturated sodium chloride solution (10 L×2). The organic layers were dried over anhydrous sodium sulfate and filtered, and the filtrate was concentrated under reduced pressure to constant weight to give compound 3 (4.50 kg, yield: 90%) as a light yellow oil. $R_f$=0.23 (petroleum ether/ethyl acetate=10:1).

$[\alpha]_D$=−123.2° (c=1.95, MeOH);
$^1$H NMR (500 MHz, CDCl$_3$) δ 4.84-4.81 (m, 1H), 4.79 (s, 1H), 4.29-4.24 (m, 1H), 3.04 (t, J=13.4 Hz, 1H), 2.83 (tt, J=12.8, 3.7 Hz, 1H), 2.49-2.35 (m, 2H), 1.92 (ddd, J=14.2, 5.5, 3.5 Hz, 1H), 1.76 (s, 3H), 1.67 (s, 3H);
$^{13}$C NMR (126 MHz, CDCl$_3$) δ 204.8, 146.6, 110.8, 77.2, 68.2, 41.3, 39.2, 33.1, 22.2, 20.5.

Step (c): The compound 3 (4.50 kg, 22.22 mol, 1 eq) and methylene chloride (12 L) were added to the 50 L reaction kettle, stirred for 8 minutes, cooled to 18 DEG C., and 4-dimethylaminopyridine (4.39 kg, 35.97 mol, 1.61 eq) was added. The p-toluenesulfonyl chloride (5.71 kg, 29.97 mol, 1.35 eq) was dissolved with methylene chloride (12 L), which was added dropwise into the reaction kettle with the inner temperature being controlled to be 15 to 25 DEG C. during the dropwise adding process. After the dropwise adding, the reaction temperature was raised to room temperature and the stirring was continued for about 12 hours. Tap water (15 L) was added to the reaction kettle for stirring and liquid separation. The organic layers were then washed with dilute hydrochloric acid (2 to 3%, 15 L) and the tap water (15 L) respectively, and were dried over anhydrous sodium sulfate, filtered, and concentrated under reduced pressure to constant weight. The methanol (20 L) was added to the residue and then was stirred for crystallization at 0 to 5 DEG C. for about 8 hours. After filtration under reduced pressure, the crystals were washed with cold methanol and dried in vacuum to give a white solid, that is, compound 4 (4.25 kg, yield 53.6%). The yield of the three steps was calculated by D(+)-carvone as 59.6% with purity 98% and 100% ee [HPLC Purity Detection Chromatography Conditions: C18 column, 5 μm, 4.6×250 mm, mobile phase water-acetonitrile=10:90, flow rate 0.5 mL/min, detection wavelength 227 nm, $t_R$=9.64 min; Enantiomer Detection Conditions: OD column, 5 μm, 4.6×250 mm, mobile phase water-methanol=15:85, flow rate 0.2 mL/min, detection wavelength 227 nm, $t_R$ (enantiomer 4)=37.4 min, $t_R$(4)=40.6 min]. $R_f$=0.54 (petroleum ether/ethyl acetate=10:1).

$[\alpha]_D$=−75.15° (c=0.83, $CH_2Cl_2$);

$^1$H NMR (500 MHz, $CDCl_3$) δ 7.77 (d, J=8.3 Hz, 2H), 7.35 (d, J=8.0 Hz, 2H), 5.03 (dd, J=3.0, 2.1 Hz, 1H), 4.79 (s, 1H), 4.69 (s, 1H), 2.97 (t, J=13.8 Hz, 1H), 2.66 (tt, J=13.1, 3.4 Hz, 1H), 2.45 (s, 3H), 2.42-2.34 (m, 2H), 2.03 (ddd, J=14.8, 5.5, 3.3 Hz, 1H), 1.65 (s, 3H), 1.47 (s, 3H);

$^{13}$C NMR (126 MHz, $CDCl_3$) δ 201.8, 145.62, 145.58, 133.8, 130.2, 127.9, 111.1, 85.3, 65.7, 40.8, 38.8, 31.2, 22.2, 21.8, 20.3.

Embodiment 2 Preparation of Intermediate Compound 7

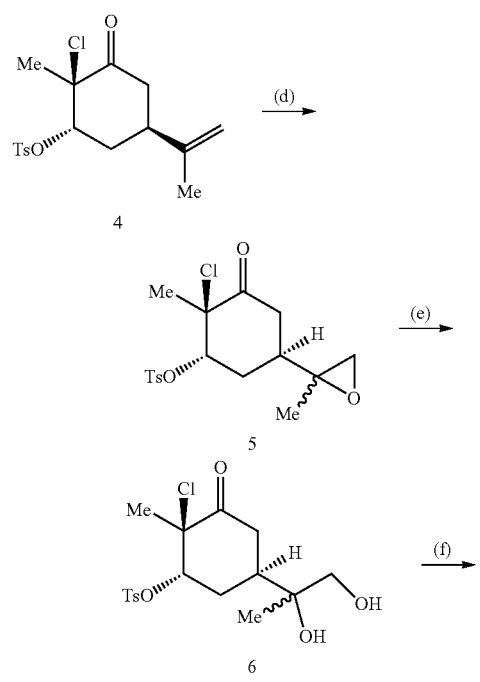

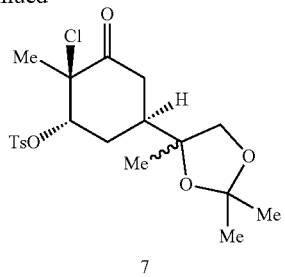

Step (d): The compound 4 (4.20 kg, 11.77 mol, 1.00 eq) and methylene chloride (21 L) were added to the 50 L reaction kettle, and was stirred and cooled to 18 DEG C. M-chloroperoxybenzoic acid (2.63 kg, 85%, 12.95 mol, 1.10 eq) was added to the reaction kettle at four times with a 30-minute interval. After that, the reaction temperature was raised to room temperature for 5 hours of stirring. The reaction liquid was cooled to 0 to 5 DEG C., stirred for 1.5 hours, and was filtered under reduced pressure. The filter cake was washed with cold methylene chloride (5 L), the saturated sodium bicarbonate solution (5 L) was slowly added to the filtrate for stirring for 30 minutes. After the liquid was separated, the aqueous layer was extracted with methylene chloride (10 L), and the organic layers were combined and filtered under reduced pressure via Buchner funnel [with a pad of silica gel (0.50 kg)]. The filter cake was washed with methylene chloride (10 L) and the filtrate was concentrated under reduced pressure to constant weight to give compound 5 (4.61 kg, yield: 105.1%) as a white solid, $R_f$=0.14 (petroleum ether/ethyl acetate=10:1).

$[\alpha]_D$=−56.9° (c=0.68, MeOH);

$^1$H NMR (500 MHz, $CDCl_3$) δ 7.76 (d, J=8.2 Hz, 2H), 7.36 (d, J=7.9 Hz, 2H), 5.05-4.99 (m, 1H), 2.86 (td, J=13.9, 9.9 Hz, 1H), 2.63 (d, J=4.4 Hz, 0.5H), 2.54 (d, J=4.4 Hz, 0.5H), 2.53 (s, 1H), 2.45 (s, 3H), 2.44-2.27 (m, 2H), 2.16-1.96 (m, 2H), 1.45 (s, 3H), 1.25 (s, 1.5H), 1.24 (s, 1.5H);

$^{13}$C NMR (126 MHz, $CDCl_3$) δ 201.1, 201.0, 145.70, 145.68, 133.6, 133.5, 130.2, 127.94, 127.89, 84.9, 84.8, 65.61, 65.55, 57.65, 57.60, 52.7, 52.6, 37.7, 37.6, 37.6, 37.5, 28.4, 28.0, 22.2, 21.8, 18.6, 18.3.

Step (e): The compound 5 (4.61 kg, 12.36 mol, 1 eq) and tetrahydrofuran (23 L) were added to the 50 L reaction kettle and stirred, sulfuric acid solution (diluting 1.15 kg concentrated sulfuric acid with 4.6 L water, 11.78 mol, 0.95 eq) was added at room temperature and was stirred at room temperature for 12 hours. Sodium bicarbonate solid (2.1 kg) was slowly added to the reaction liquid for neutralization. The stirring was continued for 30 minutes after the pH was 7 to 8. The reaction solution was filtered under reduced pressure. The filter cake was washed with tetrahydrofuran, and the filtrate was concentrated under reduced pressure. The ethyl acetate (10 L) and water (3 L) were added to the residue for stirring and liquid separation. The aqueous layer was extracted with ethyl acetate (5 L×2), the organic layers were combined, washed once with saturated aqueous sodium chloride (5 L), dried over anhydrous sodium sulfate and filtered, and concentrated under reduced pressure to give constant weight to thick compound 6 (5.10 kg, yield: 105.6%) which was directly used in the next reaction.

Step (f): The compound 6 was dissolved with methylene chloride (15 L) and transferred to the 50 L reaction kettle and stirred at room temperature. P-toluenesulfonic acid monohydrate (0.10 kg, 0.53 mol, 0.043 eq) and 2,2-dimethoxypropane (1.49 kg, 14.36 mol, 1.16 eq) were added. After that, the stirring was performed at room temperature for 1 hour. Saturated sodium carbonate solution (2 L) was added slowly and stirred for 30 minutes. After the liquid was separated, the organic layers were dried over anhydrous sodium sulfate and filtered, and the filtrate was concentrated under reduced pressure. The methanol was added to the concentrate (12 L) for 5 hours at 0 to 5 DEG C. The filtration was performed under reduced pressure. The filter cake was washed with cold methanol (5 L) and dried in vacuum to give compound 7 (3.40 kg, yield: 95.7%) as a white solid, and the yield in three steps was calculated by the intermediate 4 as 67.1% with purity 96.5%. (HPLC Purity Detection Chromatography Conditions: C18 column, 5 μm, 4.6×250 mm, mobile phase water-acetonitrile=10:90, flow rate 0.5 mL/min, detection wavelength 227 nm, $t_R$=9.14 min), $R_f$=0.21 (petroleum ether/ethyl acetate=10:1).

$[\alpha]_D$=−61.2° (c=1.22, $CH_2Cl_2$);
$^1H$ NMR (500 MHz, $CDCl_3$) δ 7.80-7.73 (m, 2H), 7.39-7.32 (m, 2H), 5.07 (s, 0.6H), 5.03 (s, 0.4H), 3.76 (d, J=8.8 Hz, 0.6H), 3.64 (d, J=8.4 Hz, 0.4H), 3.69-3.59 (m, 1H), 2.88 (t, J=13.8 Hz, 0.4H), 2.87 (t, J=13.7 Hz, 0.6H), 2.50 (d, J=14.3 Hz, 0.4H), 2.45 (s, 3H), 2.39-2.09 (m, 3.2H), 1.87 (d, J=14.4 Hz, 0.4H), 1.50 (s, 1.2H), 1.48 (s, 1.8H), 1.36 (s, 3H), 1.33 (s, 1.8H), 1.31 (s, 1.2H), 1.21 (s, 1.8), 1.19 (s, 1.2);
$^{13}C$ NMR (126 MHz, $CDCl_3$) δ 202.0, 201.7, 145.64, 145.56, 133.78, 133.76, 130.23, 130.18, 127.9, 109.89, 109.85, 85.2, 85.1, 81.6, 72.8, 72.6, 65.7, 65.6, 40.2, 40.1, 37.9, 37.2, 27.3, 27.3, 26.9, 26.83, 26.78, 22.5, 22.4, 22.21, 22.19, 21.8.

Embodiment 3 Preparation of Intermediate Compound 10 (R is Methyl)

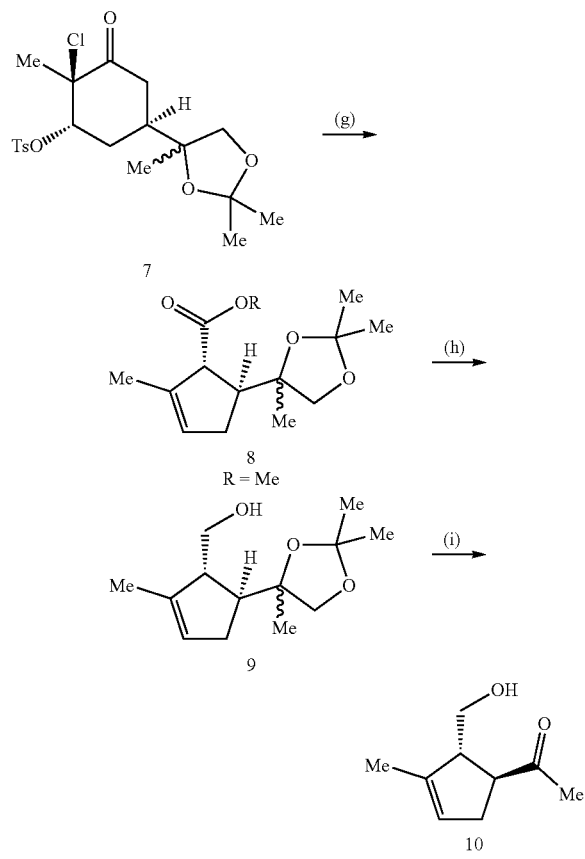

Step (g): The compound 7 (3.4 kg, 7.88 mol, 1.00 eq), methyl tertiary butyl ether (34 L) and methanol (6.8 L) were added to a 100 L reaction kettle, and stirred and cooled to 0 to 5 DEG C. Methanol solution of sodium methoxide (4.55 kg, 30% wt, 25.25 mol, 3.20 eq) was added dropwise with the inner temperature being controlled to be no more than 5 DEG C. After the dropwise adding, the reaction temperature was raised to room temperature slowly and the stirring was continued for 20 hours. The reaction liquid was cooled to 5 to 10 DEG C., and ice water (17.5 L) was slowly added dropwise. The aqueous layer was extracted with methyl tertiary butyl ether (10 L×2) after the liquid was separated, and the organic layers were combined and washed with saturated salt water (10 L×2). The organic layers were dried over anhydrous sodium sulfate after another liquid separation and were filtered under reduced pressure. The filtrate was concentrated under reduced pressure. The concentrate was dissolved with petroleum ether (8 L), filtered under reduced pressure via Buchner funnel [with a pad of silica gel (0.50 kg)] and washed with petroleum ether/ethyl acetate (25:1, 12 L), and the filtrate was concentrated under reduced pressure to give compound 8 (2.08 kg, yield: 100%) as a light yellow oil, $R_f$=0.41 (petroleum ether/ethyl acetate=10:1).

$[\alpha]_D$=+127.7° (c=0.69, MeOH);
$^1H$ NMR (400 MHz, $CDCl_3$) δ 5.47-5.39 (m, 1H), 3.81 (t, J=8.7 Hz, 1H), 3.705 (s, 1.8H), 3.700 (s, 1.2H), 3.70-3.66 (m, 1H), 3.43-3.36 (m, 0.4H), 3.36-3.29 (m, 0.6H), 3.00-2.88 (m, 1H), 2.60-2.44 (m, 1H), 2.22-2.06 (m, 1H), 1.67 (s, 1.2H), 1.65 (s, 1.8H), 1.38 (s, 1.8H), 1.37 (s, 1.8H), 1.36 (s, 1.2H), 1.35 (s, 1.2H), 1.26 (s, 1.8H), 1.22 (s, 1.2H);
$^{13}C$ NMR (126 MHz, $CDCl_3$) δ 175.7, 175.5, 137.5, 137.3, 127.5, 127.4, 109.54, 109.47, 82.9, 73.3, 72.3, 56.5, 56.1, 51.93, 51.91, 50.3, 50.2, 34.5, 34.3, 27.2, 27.1, 27.0, 26.9, 24.5, 22.4, 15.31, 15.27.

Step (h): Tetrahydrofuran (18 L) was added to the 50 L reaction kettle, stirred, and cooled to 5 DEG C. Aluminum lithium hydride (0.33 kg, 8.67 mol, 1.10 eq) was added slowly under nitrogen flow protection. The tetrahydrofuran (2 L) solution of the intermediate compound 8 (2.08 kg, 7.88 mol, 1 eq) was added dropwise to the reaction kettle with the inner temperature being controlled to be 5 to 10 DEG C. during the dropwise adding process. After the dropwise adding, the stirring was continued for 2 hours at 5 to 10 DEG C. The saturated sodium sulfate solution (1.32 L) was slowly added dropwise. After the dropwise adding, the reaction temperature was raised to room temperature and the stirring was continued for 0.5 hour. The reaction solution was filtered under reduced pressure. The filter cake was washed with tetrahydrofuran (6 L×3), and the filtrate was concentrated under reduced pressure until the total volume was about 18 L to give the tetrahydrofuran solution of compound 9, which was directly used in the next reaction.

Step (i): The tetrahydrofuran solution of compound 9 was transferred to the 50 L reaction kettle, stirred at room temperature, and then sulfuric acid solution (3.86 L, 20%, 7.88 mol, 1.00 eq) was added, and stirred at room temperature for 5 hours. The water (15 L) was added and the pH was adjusted to 7 to 8 with sodium bicarbonate solid (1.3 to 1.5 kg), and sodium periodate (1.68 kg, 7.88 mol, 1.00 eq) was added slowly in batches and stirred at room temperature for 2 hours. The reaction solution was filtered under reduced pressure. The filter cake was washed with tetrahydrofuran (3 L). The filtrate was transferred to the reaction kettle and stirred, and the anhydrous sodium sulfite (1.49 kg) was added and stirred for 0.5 hour (using the starch-KI test paper to test the absence of oxidizability). The tetrahydrofuran was concentrated under reduced pressure and recovered, and the remaining liquid was extracted with ethyl acetate (10 L×3). The organic layers were combined and washed with saturated sodium chloride (10 L), dried over anhydrous sodium sulfate, filtered and concentrated, and the crude product was chromatographically purified (eluting with petroleum ether: ethyl acetate=10:1 to 5:1) by silica gel column to give compound 10 as a light yellow oil (1.12 kg, yield: 91.8%). The yield in three steps was calculated by intermediate 7 as 91.8%. $R_f$=0.57 (petroleum ether/ethyl acetate=1:1).

$[\alpha]_D$=+105.7° (c=1.42, MeOH);

$^1$H NMR (500 MHz, CDCl$_3$) δ 5.35 (s, 1H), 3.80-3.71 (m, 1H), 3.65-3.57 (m, 1H), 3.18 (dt, J=9.7, 6.2 Hz, 1H), 2.98 (s, 1H), 2.62 (ddd, J=11.7, 10.8, 1.8 Hz, 1H), 2.50-2.39 (m, 1H), 2.19 (s, 3H), 1.68 (s, 3H);

$^{13}$C NMR (126 MHz, CDCl$_3$) δ 210.4, 138.3, 124.8, 63.9, 54.4, 52.5, 34.3, 28.4, 14.7.

Embodiment 4 Preparation of Intermediate Compound 11

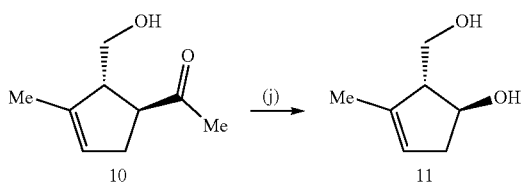 [SMILES: CC(=O)[C@H]1CC=C(C)[C@@H]1CO ; CC1=CC[C@H](O)[C@H]1CO]

Step (j): The compound 10 (1.12 kg, 7.26 mol, 1.00 eq) and methanol (40 L) were added to the 50 L reaction kettle equipped with a reflux condenser and stirred at room temperature, and hydrogen peroxide solution (1.86 kg, 30% wt, 16.41 mol, 2.26 eq) was added slowly for 30 minutes and heated to an inner temperature of 60 DEG C. The sodium hydroxide solution (2.53 L, 2.5 mol/L, 6.25 mol, 0.86 eq) was added dropwise to the reaction kettle for 80 minutes. The inner temperature was maintained at 65 to 70 DEG C. after the dropwise adding and the stirring was continued for 0.5 hour; the hydrogen peroxide solution (1.87 kg, 30% wt, 16.41 mol, 2.26 eq) and sodium hydroxide solution (2.53 L, 2.5 mol/L, 6.25 mol, 0.86 eq) were repetitively added at this temperature for 3 times, and the reaction was monitored by TLC. The reaction solution was cooled to room temperature after the raw material 10 disappeared and was extracted with ethyl acetate; the organic layers were combined and dried over anhydrous sodium sulfate. The reaction solution was filtered under reduced pressure. Triphenylphosphine (0.70 kg) was added to the filtrate, stirred for 2 hours, and concentrated under reduced pressure. The remaining product was chromatographically purified (eluting with petroleum ether:ethyl acetate=10:1 to 1:2) by silica gel column to give compound 11 (0.42 kg) as a light yellow solid with a 45% yield. $R_f$=0.19 (petroleum ether/ethyl acetate=1:1).

$[\alpha]_D$=+98.1° (c=2.63, MeOH);

$^1$H NMR (400 MHz, CDCl$_3$) δ 5.41-5.32 (m, 1H), 4.38 (dt, J=7.1, 3.7 Hz, 1H), 3.84 (dd, J=10.7, 3.9 Hz, 1H), 3.50 (dd, J=10.7, 7.6 Hz, 1H), 2.83 (brs, 2H), 2.69-2.59 (m, 1H), 2.59-2.51 (m, 1H), 2.26-2.14 (m, 1H), 1.69 (s, 3H).

$^{13}$C NMR (126 MHz, CDCl$_3$) δ 137.6, 124.5, 76.6, 63.2, 59.8, 41.1, 15.3.

Embodiment 5 Preparation of Intermediate Compound 12

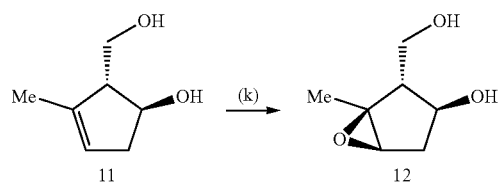 [SMILES: CC1=CC[C@H](O)[C@H]1CO ; C[C@@]12O[C@@H]1C[C@H](O)[C@H]2CO]

Step (k): The compound 11 (0.42 kg, 3.28 mol, 1.00 eq) and methylene chloride (4.20 L) were added to a 10 L reaction kettle, stirred, cooled to −5 to 0 DEG C., and vanadyl acetylacetonate (40 g, 0.15 mol, 0.046 eq) was added. The methylene chloride solution [0.52 kg, 70% wt, extracting the tert-butyl hydroperoxide aqueous solution (4.0 mol, 1.22 eq) with methylene chloride (0.8 L) and adding anhydrous magnesium sulfate to the methylene chloride layer for drying and filtration] of tert-butyl hydroperoxide was added dropwise to the reaction kettle with the inner temperature being controlled to be no more than 5 DEG C. during the dropwise adding process. The stirring was continued for 2 hours at 0 to 5 DEG C. after the dropwise adding. Anhydrous sodium sulfite (3 kg) was added, stirred for 3 hours, filtered under reduced pressure via Buchner funnel [with a pad of silica gel (0.20 kg)], washed with ethyl acetate (5 L), and the filtrate was concentrated under reduced pressure to constant weight to give compound 12 (0.45 kg, yield: 95.1%) as a yellow oil, $R_f$=0.11 (petroleum ether/ethyl acetate=1:1).

$[\alpha]_D$=+38.9° (c=1.81, MeOH);

$^1$H NMR (500 MHz, CDCl$_3$) δ 4.00 (dd, J=11.6, 6.0 Hz, 1H), 3.76 (d, J=10.6 Hz, 1H), 3.58-3.51 (m, 1H), 3.45 (s, 1H), 2.57 (d, J=11.8 Hz, 1H), 2.17-2.11 (m, 2H), 2.00 (d, J=15.2 Hz, 1H), 1.48 (s, 3H);

$^{13}$C NMR (126 MHz, CDCl$_3$) δ 74.0, 66.2, 64.3, 61.6, 54.8, 37.6, 15.6.

Embodiment 6 The Synthesis of Entecavir

1. Preparation of Intermediate Compound 14 (R1=R2=TBS)

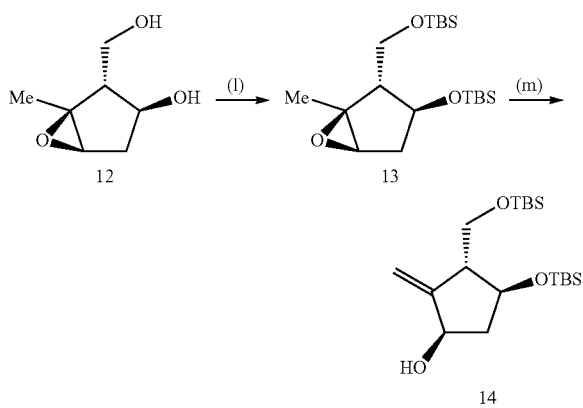

Step (l): The compound 12 (0.45 kg, 3.12 mol) and N,N-dimethylformamide (4 L), imidazole (0.49 kg, 7.21 mol, 2.31 eq), 4-dimethylaminopyridine (40 g, 0.33 mol, 0.11 eq) were added to the reaction kettle in sequence, stirred, cooled to an inner temperature of 10 to 15 DEG C. The tert-butyldimethylsilyl chloride (1.04 kg, 6.88 mol, 2.21 eq) was added to the reaction kettle at four times with a 20-minute interval. After that, the reaction temperature was raised to room temperature for 12 hours of stirring. The methyl tertiary butyl ether (8 L) and water (8 L) were added for stirring and liquid separation, and the organic layers were washed with water (5 L×3) and combined, and dried over anhydrous sodium sulfate. The reaction solution was filtered under reduced pressure. The filtrate was concentrated under reduced pressure and the remaining oil was dissolved with petroleum ether (4 L), and was filtered under reduced pressure via Buchner funnel [with a pad of silica gel (1.00 kg)] and washed with petroleum ether/ethyl acetate (150:1, 5 L). The filtrate was concentrated under reduced pressure and was chromatographically purified (eluting with petroleum ether:ethyl acetate=100% petroleum ether to 100:1) by silica gel column to give compound 13 (0.98 kg, yield: 84.3%) as a light yellow oil, $R_f$=0.69 (petroleum ether/ethyl acetate=10:1).

$[\alpha]_D$=+31.5° (c=1.31, MeOH);
$^1$H NMR (500 MHz, CDCl$_3$) δ 4.27 (d, J=7.6 Hz, 1H), 3.68 (d, J=3.6 Hz, 2H), 3.25 (s, 1H), 2.10 (ddd, J=14.6, 7.6, 1.4 Hz, 1H), 2.02 (s, 1H), 1.83 (d, J=14.6 Hz, 1H), 1.41 (s, 3H), 0.89 (s, 9H), 0.87 (s, 9H), 0.050 (s, 3H), 0.054 (s, 3H), 0.03 (s, 6H);
$^{13}$C NMR (126 MHz, CDCl$_3$) δ 76.5, 66.0, 64.8, 62.6, 55.3, 39.0, 26.0, 25.8, 18.2, 18.1, 16.1, -4.4, -4.5, -5.6, -5.7.

Step (m): 2,2,6,6-tetramethylpiperidine (0.48 kg, 3.42 mol, 1.30 eq) and toluene (8 L) were added to a 20 L 4-neck reaction flask under nitrogen protection, and stirred and cooled to -8 DEG C. N-hexane solution of N-butyllithium (1.37 L, 2.5 mol/L, 3.42 mol, 1.30 eq) was added dropwise with the inner temperature being no more than 10 DEG C. during the dropwise adding process for 2 hours. After the dropwise adding, the stirring was performed for 1 hour with the temperature maintained at -10 to 0 DEG C. N-hexane solution of diethylaluminum chloride (1.71 L, 2.0 mol/L, 3.42 mol, 1.30 eq) was added dropwise with the inner temperature being no more than 0 DEG C. during the dropwise adding process for 2 hours. After the dropwise adding, the stirring was performed for 1.5 hours with the temperature maintained at -10 to 0 DEG C. The toluene (2 L) solution of the compound 13 (0.98 kg, 2.63 mol, 1.0 eq) was added dropwise to the reaction flask for about 2 hours. After the dropwise adding, the stirring was performed for 3 hours with the temperature maintained at -5 to 0 DEG C. Saturated potassium sodium tartrate solution (0.6 L) was slowly added dropwise. After the dropwise adding, the stirring was continued for 1 hour, and filtration was performed under reduced pressure. The filter cake was washed with ethyl acetate (5 L), and the combined filtrates were washed with water (3 L×3). The organic layers were concentrated under reduced pressure and the remaining oil was chromatographically purified (eluting with petroleum ether:ethyl acetate=100% petroleum ether to 25:1) by silica gel column to give compound 14 (0.91 kg, yield: 92.8%, 100% ee) as a yellow solid [Enantiomer Detection Conditions: OD column, 5 μm, 4.6×250 mm, mobile phase water-acetonitrile=20:80, flow rate 0.3 mL/min, detection wavelength 211 nm, $t_R$ (enantiomeric 14)=16.27 min, $t_R$(14)=18.46 min]. The yield in three steps was calculated by intermediate 11 as 74.5%. $R_f$=0.43 (petroleum ether/ethyl acetate=10:1).

$[\alpha]_D$=-51.9° (c=1.07, MeOH);
$^1$H NMR (500 MHz, CDCl$_3$) δ 5.38 (s, 1H), 5.13 (s, 1H), 4.38-4.30 (m, 2H), 3.57 (dd, J=10.2, 5.1 Hz, 1H), 3.32 (t, J=9.3 Hz, 1H), 2.88 (d, J=10.5 Hz, 1H), 2.80-2.71 (m, 1H), 1.99 (dt, J=13.5, 4.9 Hz, 1H), 1.82 (d, J=13.6 Hz, 1H), 0.89 (s, 18H), 0.09 (s, 6H), 0.04 (s, 3H), 0.03 (s, 3H);
$^{13}$C NMR (126 MHz, CDCl$_3$) δ 154.6, 111.8, 75.7, 75.5, 64.9, 55.2, 42.3, 26.1, 26.0, 18.5, 18.1, -4.6, -4.7, -5.3, -5.4.

2. Preparation of Intermediate Compound 15

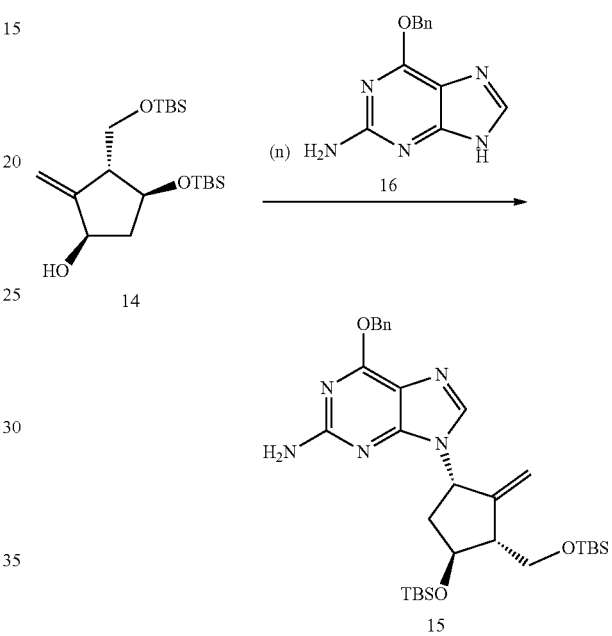

Step (n): The compound 14 (180 g, 0.483 mol, 1.00 eq), the compound 16 (169 g, 0.700 mol, 1.45 eq), triphenylphosphine (253 g, 0.966 mol, 2.00 eq) and dry tetrahydrofuran (1.8 L) were added to a 2 L 4-neck reaction flask under nitrogen protection and stirred with the inner temperature being cooled to 0 to 5 DEG C. Diisopropyl azodicarboxylate (169 g, 0.966 mol, 2.00 eq) was added dropwise with the inner temperature being controlled to be no more than 5 DEG C. After the dropwise adding, the stirring was continued for 2 to 3 hours at 0 to 5 DEG C. After concentration under reduced pressure, the residue was dissolved by adding ethyl acetate (200 ml), and petroleum ether (2 L) was added for crystallization after stirring for 4 to 5 hours. The filtration was performed under reduced pressure via Buchner funnel. The filter cake was washed with petroleum ether-ethyl acetate (10:1, 2 L) and the filtrate was concentrated under reduced pressure to constant weight. The residue was chromatographically purified (eluting with petroleum ether:ethyl acetate=20:1 to 10:1) by silica gel column to give compound 15 (235 g) as a light yellow foam with a yield of 81.6%. $R_f$=0.68 (petroleum ether/ethyl acetate=2:1).

$[\alpha]_D$=+17.6° (c=1.00, MeOH);
$^1$H NMR(400 MHz, Chloroform-d) δ 7.65 (s, 1H), 7.51 (d, J=7.36 Hz, 2H), 7.39-7.27 (m, 3H), 5.56 (s, 2H), 5.51 (t, J=8.08 Hz, 1H), 5.16 (s, 1H), 4.84 (s, 2H), 4.83 (d, J=2.6 Hz, 1H), 4.47-4.38 (m, 1H), 3.84-3.71 (m, 2H), 2.66 (s, 1H), 2.28 (td, J=11.38, 9.24, 4.84 Hz, 1H), 2.21-2.12 (m, 1H), 0.92 (s, 9H), 0.90 (s, 9H), 0.11-0.04 (m, 12H).

$^{13}$C NMR (126 MHz, Chloroform-d) δ 161.1, 159.1, 154.5, 149.4, 138.9, 136.7, 128.49, 128.45, 128.1, 115.8, 111.2, 72.5, 68.1, 64.2, 56.0, 54.9, 40.6, 26.2, 26.0, 18.6, 18.2, −4.4, −4.6, −5.2, −5.3.

3. The Synthesis of Entecavir

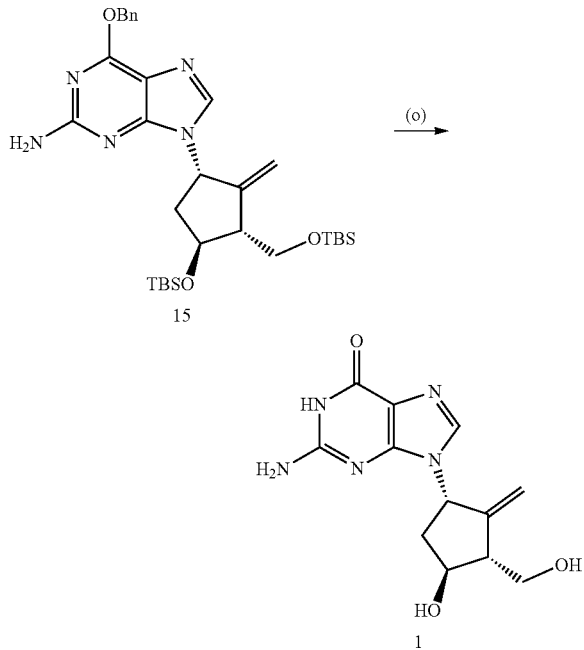

Step (o): The compound 15 (200 g, 0.335 mol, 1.00 eq) and tetrahydrofuran (1.34 L) were added to a 2 L three-neck flask equipped with the reflux condenser, stirred and dissolved at room temperature, and heated to an inner temperature of 55 DEG C. and stirred for 6 hours after adding diluted hydrochloric acid (1.34 L, 2.5 mol/L, 3.360 mol, 10.00 eq). The reaction liquid was concentrated under reduced pressure to remove tetrahydrofuran, and the ethyl acetate (0.5 L×3) was added to the remaining aqueous solution for extraction. The aqueous layer was cooled to 5 to 10 DEG C. The sodium hydroxide solution (6 mol/L, about 0.6 L) was added for neutralization. The stirring was continued for 5 hours for crystallization after the pH was adjusted to 7 to 8 and perform the filtration under reduced pressure; the filter cake was washed with cold water (300 ml) and 95% ethanol (200 ml) respectively, and the solid was collected. The filtrate was concentrated to a volume of 300 to 400 ml under reduced pressure, the stirring was continued for 10 hours for crystallization, filtration was performed under reduced pressure, and the filter cake was washed with cold water (150 ml) and 95% ethanol (100 ml) respectively. The solid was collected and combined, dried in vacuum for 5 hours at 45 DEG C. to give Entecavir crude product (86 g) with purity 98% and 100% ee. The crude product was recrystallized from pure water to give entecavir monohydrate (72 g), in which HPLC purity was more than 99.7%, any individual impurity was less than 0.1%, and the yield was 79.3%. [HPLC Chromatographic Conditions: C18 column, 5 μm, 4.6×250 mm, mobile phase A was acetonitrile-water (3:97), mobile phase B was acetonitrile, and gradient was 0 to 8 min, 100% A; 8 to 25 min, 100 to 70% A; 25 to 30 min, 70 to 20% A; 30 to 32 min, 20 to 10% A, 32 to 55 min, 10% A; 55 to 56 min, 10 to 100% A; 56 to 65 min, 100% A. Flow rate 1.0 mL/min, detection wavelength 254 nm, $t_R$ (entecavir)=15.8 min; Enantiomer Detection Conditions: AD Column, 5 μm, 4.6× 250 mm, mobile phase was N-hexane:ethanol:methanol: triethylamine (60:20:20:0.1), flow rate 1.0 mL/min, detection wavelength 254 nm, $t_R$ (enantiomer)=8.1 min, $t_R$ (entecavir)=12.9 min].

$^1$H NMR (500 MHz, DMSO) δ 10.55 (s, 1H), 7.65 (s, 1H), 6.40 (s, 2H), 5.36 (dd, J=10.3, 8.0 Hz, 1H), 5.10 (s, 1H), 4.85 (d, J=3.1 Hz, 1H), 4.81 (t, J=5.3 Hz, 1H), 4.56 (s, 1H), 4.23 (s, 1H), 3.54 (t, J=6.1 Hz, 2H), 2.55-2.50 (m, 1H), 2.26-2.17 (m, 1H), 2.04 (dd, J=12.5, 7.8 Hz, 1H);

$^{13}$C NMR (126 MHz, DMSO) δ 156.8, 153.4, 151.4, 151.3, 135.9, 116.2, 109.2, 70.4, 63.0, 55.1, 54.1, 39.2.

The above-described various technical features of the embodiments can be combined in various ways. The above-described embodiments do not describe all the possible combinations of the technical features to provide a concise description. However, those combinations which are not described should be within the scope of the description as long as no contradiction occurs in the combinations of these technical features.

The above-described embodiments represent only several embodiments of the present invention, which are described in specific detail but should not be construed as limitations on the scope of the claims. It should be noted that modifications and improvements can be made for those skilled in the art without departing from the spirit of the invention, all of which fall within the scope of the present invention. Accordingly, the scope of the present invention should be subject to the appended claims.

The invention claimed is:

1. An entecavir intermediate, wherein the entecavir intermediate is selected from the following compounds

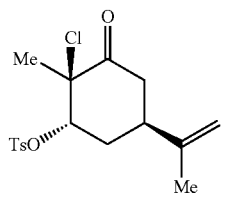

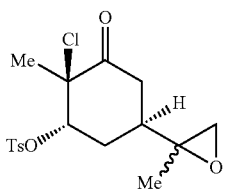

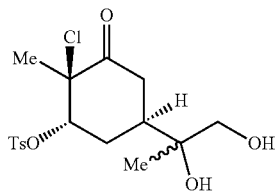

-continued

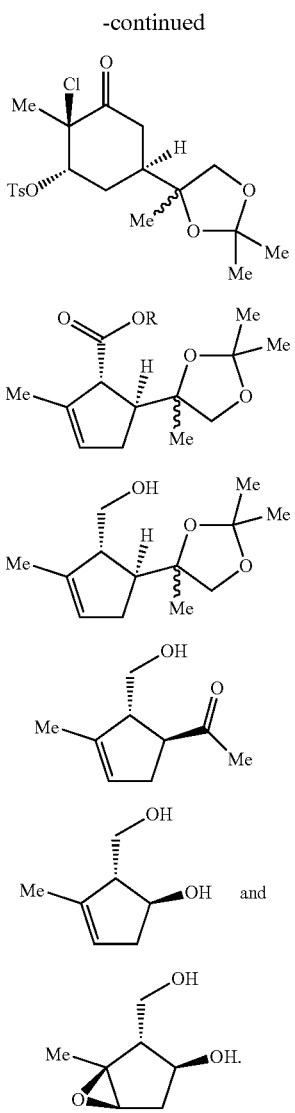

wherein R is methyl or ethyl.

2. A synthetic method for the entecavir intermediate having the structure shown in Formula 10, comprising the following steps of:
(c) reacting the compound of Formula 3 with an esterification reagent in the presence of a base to produce the compound of Formula 4;
(d) epoxide reacting the compound of Formula 4 in the presence of an epoxide reagent to produce the compound of Formula 5;
(e) epoxide ring-opening reacting the compound of Formula 5 under the action of an acid to produce the compound of Formula 6;
(f) dihydroxy acetone reacting the compound of Formula 6 with a hydroxyl acetonide protection reagent under the action of an acid catalyst to produce the compound of Formula 7;
(g) Favorskii rearrangement reacting the compound of Formula 7 under the action of the base to produce the compound of Formula 8;
(h) reduction reacting the compound of Formula 8 under the action of a reducing agent to produce the compound of Formula 9;
(i) removing the hydroxyl protecting group of the compound of Formula 9 under the catalysis of the acid, and oxidation reacting the compound of Formula 9 under the action of an oxidizing agent to produce the compound of Formula 10; and
the reaction formulas are as follows:

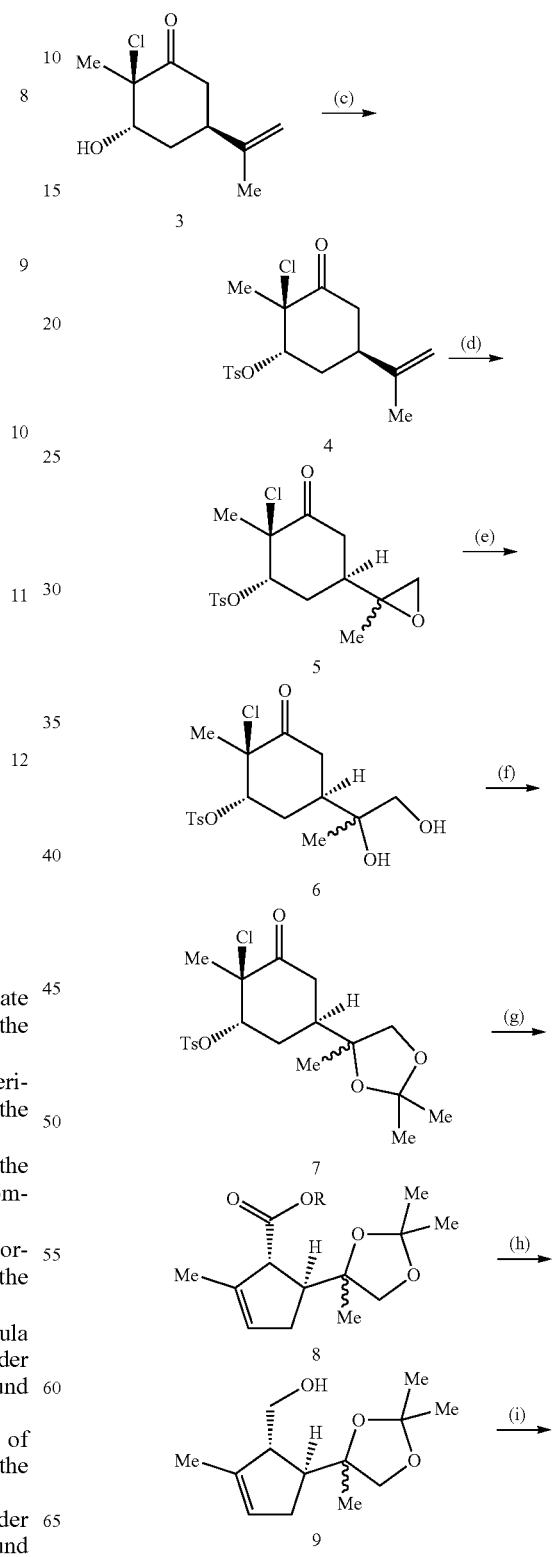

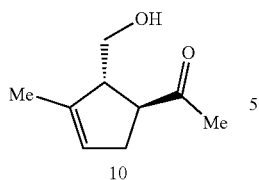

wherein R is methyl or ethyl.

3. The synthetic method for the entecavir intermediate having the structure shown in Formula 10 according to claim 2, further comprising the following steps of:
(a) epoxide reacting a D(+)-carvone under the action of the base and the oxidizing agent to produce the compound of Formula 2;
(b) chlorination ring-opening reacting the compound of Formula 2 under the action of the acid and a chloride reagent to produce the compound of Formula 3; and the reaction formulas are as follows:

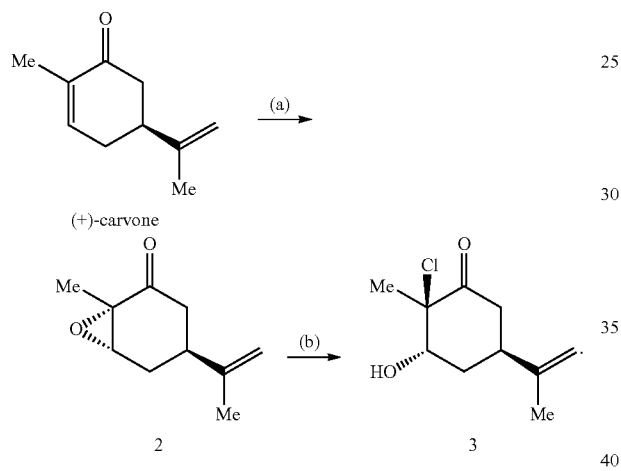

4. The synthetic method for the entecavir intermediate having the structure shown in Formula 10 according to claim 3, wherein the reaction solvent in step (a) is methanol, the base is sodium hydroxide, the oxidizing agent is hydrogen peroxide, reaction temperature of the epoxide reaction is −5 to 10 DEG C., and molar ratio of the D(+)-carvone, the base and the oxidizing agent is 1:(0.1 to 0.3): (0.8 to 1.4); and/or
the reaction solvent in step (b) is tetrahydrofuran, the acid is trifluoroacetic acid, the chloride reagent is anhydrous lithium chloride, the reaction temperature of the chlorination ring-opening reaction is 0 to 35 DEG C., and the molar ratio of the compound of Formula 2, the acid and the chloride reagent is 1:(0.8 to 2):(0.8 to 2).

5. The synthetic method for the entecavir intermediate having the structure shown in Formula 10 according to claim 2, wherein the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or
the reaction solvent in step (e) is a combination of water and organic solvent, the organic solvent is tetrahydrofuran and/or 1,4-dioxane, the volume ratio of water to organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or
the reaction in step (f) is carried out in the absence of a solvent, or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or
the reaction solvent in step (g) is an alcohol solvent or a combination of the alcohol solvent and an ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or
the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or
the reaction solvent in step (i) is selected from methanol, ethanol, tetrahydrofuran, 1,4-dioxane and water, the acid is selected from p-toluenesulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2): (0.8 to 3).

6. A synthetic method for the entecavir intermediate having the structure shown in Formula 12, comprising the following steps of:
(j) Baeyer-Villiger oxidative rearrangement reacting the compound of Formula 10 under the action of a base and peroxide to produce the compound of Formula 11;
(k) epoxide reacting the compound of Formula 11 under the action of a catalyst and an oxidizing agent to produce the compound of Formula 12; and the reaction formulas are as follows:

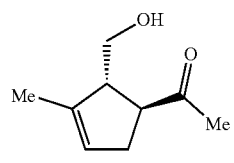

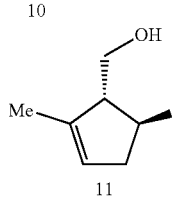 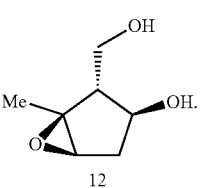

7. The synthetic method for the entecavir intermediate having the structure shown in Formula 12 according to claim 6, comprising the following steps of:

(c) reacting the compound of Formula 3 with an esterification reagent in the presence of the base to produce the compound of Formula 4;

(d) epoxide reacting the compound of Formula 4 in the presence of an epoxide reagent to produce the compound of Formula 5;

(e) epoxide ring-opening reacting the compound of Formula 5 under the action of an acid to produce the compound of Formula 6;

(f) dihydroxy acetone reacting the compound of Formula 6 with a hydroxyl acetonide protection reagent under the action of an acid catalyst to produce the compound of Formula 7;

(g) Favorskii rearrangement reacting the compound of Formula 7 under the action of the base to produce the compound of Formula 8;

(h) reduction reacting the compound of Formula 8 under the action of a reducing agent to produce the compound of Formula 9;

(i) removing the hydroxyl protecting group of the compound of Formula 9 under the catalysis of the acid, and then oxidation reacting under the action of the oxidizing agent to produce the compound of Formula 10;

(j) Baeyer-Villiger oxidative rearrangement reacting the compound of Formula 10 under the action of the base and peroxide to produce the compound of Formula 11;

(k) epoxide reacting the compound of Formula 11 under the action of the catalyst and the oxidizing agent to produce the compound of Formula 12; and the reaction formulas are as follows:

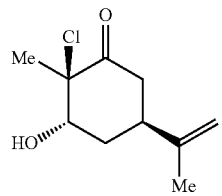

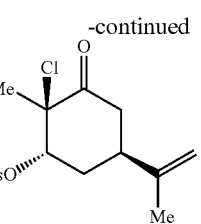

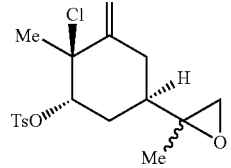

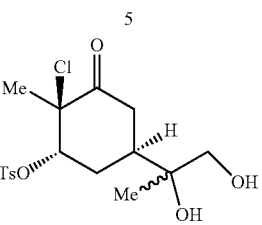

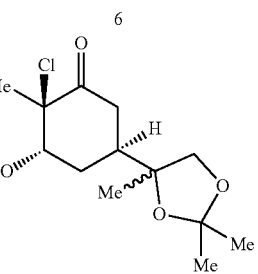

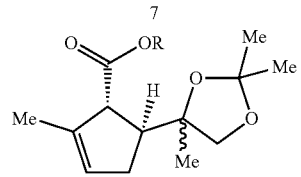

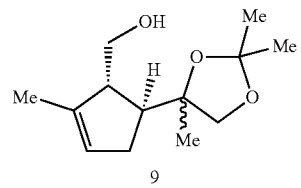

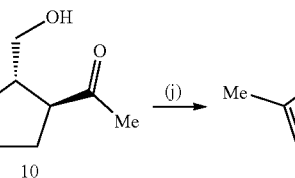

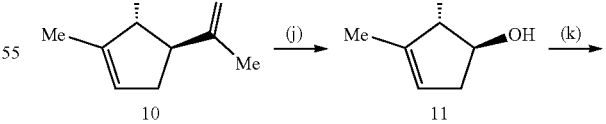

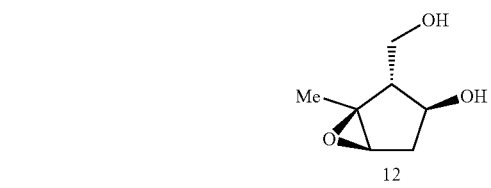

wherein R is methyl or ethyl.

8. The synthetic method for the entecavir intermediate having the structure shown in Formula 12 according to claim 7, further comprising the following steps of:
(a) epoxide reacting a D(+)-carvone under the action of the base and the oxidizing agent to produce the compound of Formula 2;
(b) chlorination ring-opening reacting the compound of Formula 2 under the action of the acid and a chloride reagent to produce the compound of Formula 3; and the reaction formulas are as follows:

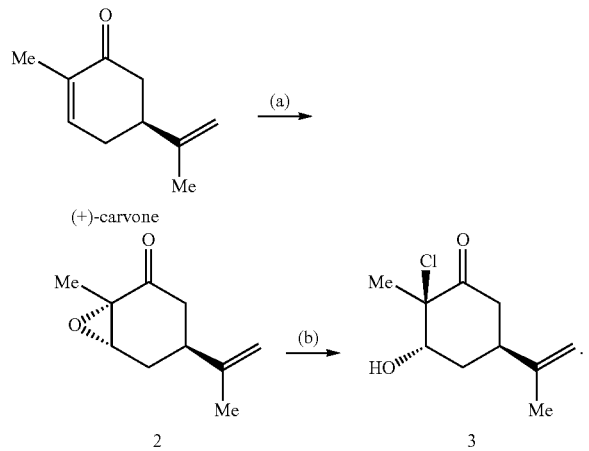

9. The synthetic method for the entecavir intermediate having the structure shown in Formula 12 according to claim 8, wherein reaction solvent in step (a) is methanol, the base is sodium hydroxide, the oxidizing agent is hydrogen peroxide, the reaction temperature of the epoxide reaction is −5 to 10 DEG C., and the molar ratio of the D(+)-carvone, the base and the oxidizing agent is 1:(0.1 to 0.3):(0.8 to 1.4); and/or
the reaction solvent in step (b) is tetrahydrofuran, the acid is trifluoroacetic acid, the chloride reagent is anhydrous lithium chloride, the reaction temperature of the chlorination ring-opening reaction is 0 to 35 DEG C., and the molar ratio of the compound of Formula 2, the acid and the chloride reagent is 1:(0.8 to 2):(0.8 to 2).

10. The synthetic method for the entecavir intermediate having the structure shown in Formula 12 according claim 6, wherein the reaction solvent in step (j) is selected from methanol, ethanol, tert-butanol and isopropanol, the base is sodium hydroxide and/or potassium hydroxide, the peroxide is selected from hydrogen peroxide, hydrogen peroxide complex and tert-butyl hydroperoxide, the temperature of the Baeyer-Villiger oxidative rearrangement reaction is 0 to 100 DEG C., and the molar ratio of the compound of Formula 10, the base and the peroxide is 1:(1 to 20):(1 to 20); and/or
the reaction solvent in step (k) is selected from dichloromethane, toluene and 1,2-dichloroethane, the catalyst is vanadyl acetylacetonate, the oxidizing agent is tert-butyl hydroperoxide, the reaction temperature of the epoxide reaction is −25 to 25 DEG C., and the molar ratio of the compound of Formula 11, the catalyst and the oxidizing agent is 1:(0.001 to 0.2):(1 to 2).

11. The synthetic method for the entecavir intermediate having the structure shown in Formula 12 according to claim 7, wherein the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or
the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or
the reaction solvent in step (e) is a combination of water and organic solvent, the organic solvent is tetrahydrofuran and/or 1,4-dioxane, the volume ratio of water to organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or
the reaction in step (f) is carried out in the absence of a solvent or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or
the reaction solvent in step (g) is an alcohol solvent or a combination of the alcohol solvent and an ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or
the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or
the reaction solvent in step (i) is selected from methanol, ethanol, tetrahydrofuran, 1,4-dioxane and water, the acid is selected from p-toluenesulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2):(0.8 to 3).

12. A synthetic method for entecavir, comprising the following steps of:

(l) protecting hydroxyl in the compound of Formula 12 to produce the compound of Formula 13;
(m) epoxide isomerization reacting the compound of Formula 13 with an epoxide isomerization reagent to produce the compound of Formula 14;
(n) reacting the compound of Formula 14 with the compound of Formula 16 under Mitsunobu reaction conditions to produce the compound of Formula 15;
(o) carrying out a hydrolysis reaction on the compound of Formula 15, removing the hydroxyl protecting group and the amino protecting group thereof, and producing the compound of Formula 1 to give entecavir; and
the reaction formulas are as follows:

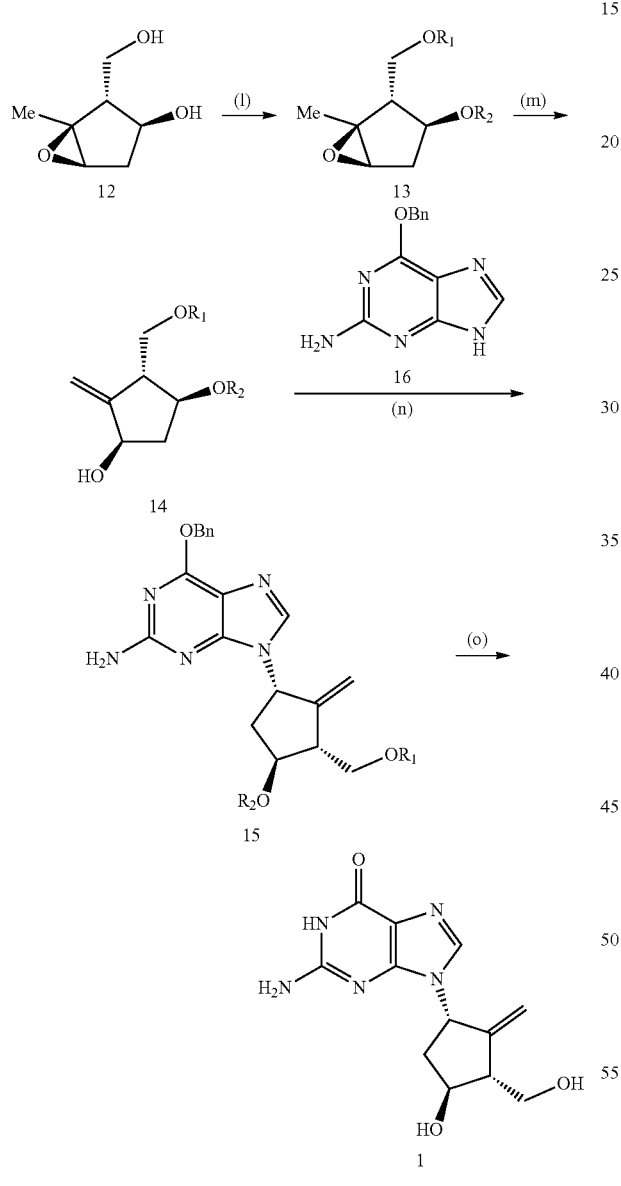

wherein R1 and R2 are protecting groups of the hydroxyl, and R1 and R2 are each independently selected from the protecting groups of the following classes: (1) silicyl, (2) alkyl, (3) alkoxymethyl, (4) benzyloxymethyl and substituted benzyloxymethyl, (5) alkoxyethyl, (6) benzyl and benzyl substituted by a phenyl ring, (7) acyl, (8) alkoxyacyl, and (9) siloxymethyl.

13. The synthetic method for entecavir according to claim 12, further comprising the following steps of:
(c) reacting the compound of Formula 3 with an esterification reagent in the presence of the base to produce the compound of Formula 4;
(d) epoxide reacting the compound of Formula 4 in the presence of an epoxide reagent to produce the compound of Formula 5;
(e) epoxide ring-opening reacting the compound of Formula 5 under the action of an acid to produce the compound of Formula 6;
(f) dihydroxy acetone reacting the compound of Formula 6 with a hydroxyl acetonide protection reagent under the action of an acid catalyst to produce the compound of Formula 7;
(g) Favorskii rearrangement reacting the compound of Formula 7 under the action of the base to produce the compound of Formula 8;
(h) reduction reacting the compound of Formula 8 under the action of a reducing agent to produce the compound of Formula 9;
(i) removing a hydroxyl protecting group of the compound of Formula 9 under the catalysis of the acid, and then oxidation reacting under the action of the oxidizing agent to produce the compound of Formula 10;
(j) Baeyer-Villiger oxidative rearrangement reacting the compound of Formula 10 under the action of the base and peroxide to produce the compound of Formula 11;
(k) epoxide reacting the compound of Formula 11 under the action of the catalyst and the oxidizing agent to produce the compound of Formula 12; and
the reaction formulas are as follows:

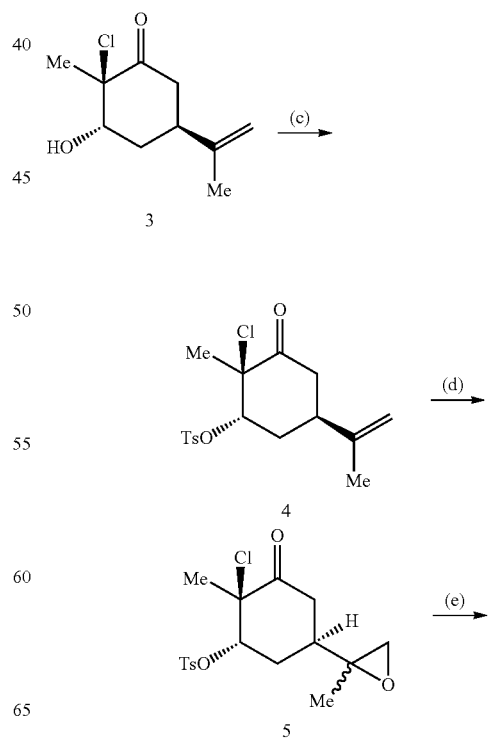

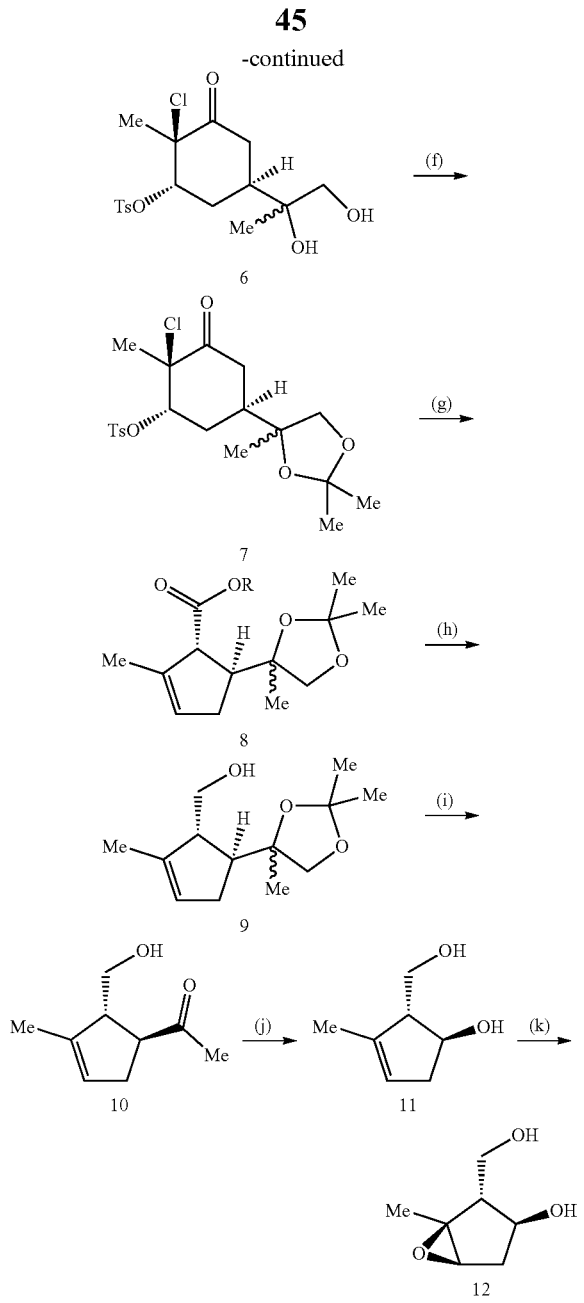

wherein R is methyl or ethyl.

14. The synthetic method for entecavir according to claim 12, wherein R 1 and R 2 are each independently selected from: trimethylsilyl, tert-butyldiphenylsilyl, tert-butyldimethylsilyl, triethylsilyl, triisopropylsilyl, methyl, methoxymethyl, 2-methoxyethoxymethyl, benzyloxymethyl, p-methoxybenzyloxymethyl, p-nitrobenzyloxym ethyl, o-nitrobenzyloxymethyl, 2-(trimethylsilyl)ethoxymethyl, tetrahydropyran-2-yl, 1-ethoxyethyl, benzyl, p-methoxybenzyl, 3,4-dimethoxybenzyl, trityl, formyl, acetyl, benzoyl, p-phenylbenzoyl, methoxyacyl, ethoxyacyl, 9-fluorenylmethoxyacyl, and tert-butoxyacyl.

15. The synthetic method for entecavir according to claim 12, wherein protecting the hydroxyl in the compound of Formula 12 in step (I) comprising: reacting the compound of Formula 12 with a hydroxyl protection reagent; R1 and R2 are each independently selected from: trimethylsilyl, tert-butyldiphenylsilyl, tert-butyldimethylsilyl, triethylsilyl, triisopropylsilyl, methyl, methoxymethyl, 2-methoxyethoxymethyl, benzyloxymethyl, p-methoxybenzyloxym ethyl, p-nitrobenzyloxymethyl, o-nitrobenzyloxymethyl, 2-(trimethylsilyl)ethoxymethyl, benzyl, p-methoxybenzyl, 3,4-dimethoxybenzyl, trityl, formyl, acetyl, benzoyl, p-phenylbenzoyl, methoxyacyl, ethoxyacyl, 9-fluorenylmethoxyacyl, and tert-butoxyacyl, the hydroxyl protection reagent is R1X and R2X, wherein X is a leaving group and is selected from halogen or triflate, reacting the compound of Formula 12 with the hydroxyl protection reagent is reacting the compound of Formula 12 with R1X and R2X in the presence of the base and/or the catalyst, the base is selected from at least one of triethylamine, diisopropylethylamine, imidazole, pyridine, sodium hydroxide, potassium hydroxide, sodium hydride, lithium hydride, sodium bis(trimethylsilyl)amide, and lithium bis(trimethylsilyl)amide, and the catalyst is selected from at least one of 4-dimethylaminopyridine, tetrabutylammonium bromide, tetrabutylammonium hydrogen sulfate and tetrabutylammonium iodide; or R1 and R2 are each independently selected from tetrahydropyran-2-yl, the hydroxyl protection reagent is dihydropyran, reacting the compound of Formula 12 with the hydroxyl protection reagent is reacting the compound of Formula 12 with the dihydropyran under acid catalysis, and the acid is selected from p-toluene sulfonic acid and pyridinium p-toluenesulfonate; or R1 and R2 are each independently selected from 1-ethoxyethyl, the hydroxyl protection reagent is ethyl vinyl ether, reacting the compound of Formula 12 with the hydroxyl protection reagent is reacting the compound of Formula 12 with the ethyl vinyl ether under acid catalysis, and the acid is selected from the p-toluene sulfonic acid and the pyridinium p-toluenesulfonate.

16. The synthetic method for entecavir according to claim 15, wherein the hydroxyl protection reagent in step (I) is tert-butyldimethylsilyl chloride, the compound of Formula 12 reacts with the hydroxyl protection reagent under the action of the base and the catalyst, the reaction solvent is selected from methylene chloride and N,N-dimethylformamide, the base is selected from triethylamine and imidazole, the catalyst is 4-dimethylaminopyridine, the reaction temperature is 0 to 50 DEG C., and the molar ratio of the compound of Formula 12, the base, the catalyst and the tert-butyldimethylsilyl chloride is 1:(2 to 3):(0.05 to 0.2):(2 to 3).

17. The synthetic method for entecavir according to claim 12, wherein the reaction solvent in step (m) is selected from toluene, xylene, tetrahydrofuran, methyl tertiary butyl ether and diethyl ether, the epoxide isomerization reagent is selected from lithium diisopropylamide, 2,2,6,6-tetramethylpiperidine lithium, aluminum complexes generated in situ by lithium diisopropylamide and diethylaluminum chloride, aluminum complexes generated in situ by 2,2,6,6-tetramethylpiperidine lithium and diethylaluminum chloride, aluminum isopropoxide, camphorsulfonic acid, p-methylbenzene sulfonic acid, and the reaction temperature of the epoxide isomerization reaction is −25 to 110 DEG C.

18. The synthetic method for entecavir according to claim 17, wherein the reaction solvent in step (m) is toluene, the epoxide isomerization reagent is the aluminum complexes generated in situ by 2,2,6,6-tetramethylpiperidine lithium and diethylaluminum chloride, the reaction temperature of the epoxide isomerization reaction is −10 to 5 DEG C., and the molar ratio of the compound of Formula 13 to the epoxide isomerization reagent is 1:(1 to 3).

19. The synthetic method for entecavir according to claim 12, wherein the molar ratio of the compound of Formula 14 to the compound of Formula 16 in step (n) is 1:(1 to 2); and/or R1 and R2 are both tert-butyldimethylsilyl, the reaction solvent of the hydrolysis reaction in step (o) is tetrahydrofuran and water, the hydrolysis reaction is carried out under the action of dilute hydrochloric acid, and the reaction temperature is 10 to 70 DEG C.

20. The method for synthesizing entecavir according to claim 12, wherein the reaction solvent in step (c) is selected from at least one of methylene chloride, 1,2-dichloroethane, chloroform, water, ethyl acetate, diethyl ether, methyl tertiary butyl ether and tetrahydrofuran, the base is selected from 4-dimethylaminopyridine or a combination of 4-dimethylaminopyridine with other bases, the esterification reagent is p-toluenesulfonyl chloride, the reaction temperature of the reaction is 0 to 50 DEG C., and the molar ratio of the compound of Formula 3, 4-dimethylaminopyridine, other bases and p-toluenesulfonyl chloride is 1:(0.5 to 10):(0 to 3):(1 to 3); and/or the reaction solvent in step (d) is dichloromethane, the temperature of the epoxide reaction is 0 to 40 DEG C., the epoxide reagent is selected from at least one of meta-chloroperoxybenzoic acid, peroxyacetic acid and trifluoroperacetic acid, and the molar ratio of the compound of Formula 4 to the epoxide reagent is 1:(1 to 2); and/or the reaction solvent in step (e) is a combination of water and organic solvent, the organic solvent is tetrahydrofuran and/or 1,4-dioxane, the volume ratio of water to the organic solvent is 1:(1 to 10), the acid is sulfuric acid, the temperature of the epoxide ring-opening reaction is 0 to 50 DEG C., and the molar ratio of the compound of Formula 5 to the acid is 1:(0.5 to 2); and/or the reaction in step (f) is carried out in the absence of a solvent or the reaction solvent in step (f) is methylene chloride, the hydroxyl acetonide protection reagent is selected from 2,2-dimethoxypropane or acetone, the acid catalyst is selected from at least one of p-toluene sulfonic acid, camphorsulfonic acid and sulfuric acid, the reaction temperature of the dihydroxy acetone reaction is 0 to 50 DEG C., and the molar ratio of the compound of Formula 6, the hydroxyl acetonide protection reagent and the acid catalyst is 1:(1 to 5):(0.01 to 0.2); and/or the reaction solvent in step (g) is an alcohol solvent or a combination of the alcohol solvent and an ether solvent, the alcohol solvent is selected from methanol and ethanol, the ether solvent is selected from diethyl ether, methyl tertiary butyl ether, tetrahydrofuran and 1,4-dioxane, the base is selected from sodium methoxide, sodium ethoxide, sodium hydroxide, potassium hydroxide, lithium hydroxide, potassium carbonate and cesium carbonate, the reaction temperature of the Favorskii rearrangement reaction is −20 to 50 DEG C., and the molar ratio of the compound of Formula 7 to the base is 1:(2 to 5); and/or the reaction solvent in step (h) is selected from tetrahydrofuran, methyl tertiary butyl ether, toluene and 1,4-dioxane, the reducing agent is selected from lithium aluminum hydride, sodium bis(2-methoxyethoxy)aluminumhydride, diisobutylaluminum hydride, sodium borohydride, potassium borohydride, lithium borohydride and lithium triethylborohydride, the reaction temperature of the reduction reaction is −20 to 60 DEG C., and the molar ratio of the compound of Formula 8 to the reducing agent is 1:(1 to 3); and/or the reaction solvent in step (i) is selected from methanol, ethanol, tetrahydrofuran, 1,4-dioxane and water, the acid is selected from p-toluene sulfonic acid, dilute hydrochloric acid, dilute sulfuric acid and acetic acid, the oxidizing agent is selected from sodium periodate, periodic acid, lead tetraacetate and potassium permanganate, the reaction temperature is 0 to 80 DEG C., and the molar ratio of the compound of Formula 9, the acid and the oxidizing agent is 1:(0.1 to 2):(0.8 to 3); and/or the reaction solvent in step (j) is selected from methanol, ethanol, tert-butanol and isopropanol, the base is sodium hydroxide and/or potassium hydroxide, the peroxide is selected from hydrogen peroxide, hydrogen peroxide complex and tert-butyl hydroperoxide, the temperature of the Baeyer-Villiger oxidative rearrangement reaction is 0 to 100 DEG C., and the molar ratio of the compound of Formula 10, the base and the peroxide is 1:(1 to 20):(1 to 20); and/or the reaction solvent in step (k) is selected from dichloromethane, toluene and 1,2-dichloroethane, the catalyst is vanadyl acetylacetonate, the oxidizing agent is tert-butyl hydroperoxide, the reaction temperature of the epoxide reaction is −25 to 25 DEG C., and the molar ratio of the compound of Formula 11, the catalyst and the oxidizing agent is 1:(0.001 to 0.2):(1 to 2).

* * * * *

UNITED STATES PATENT AND TRADEMARK OFFICE
CERTIFICATE OF CORRECTION

PATENT NO. : 11,046,663 B2
APPLICATION NO. : 16/759159
DATED : June 29, 2021
INVENTOR(S) : Yehua et al.

Page 1 of 1

It is certified that error appears in the above-identified patent and that said Letters Patent is hereby corrected as shown below:

In the Claims

Column 45, Line 56, delete "p-nitrobenzyloxym ethyl," and insert --p-nitrobenzyloxymethyl,--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*